(12) United States Patent
Boechat et al.

(10) Patent No.: US 8,436,027 B2
(45) Date of Patent: May 7, 2013

(54) AZOLE COMPOUNDS USED AS TUBERCULOSTATIC AND LEISHMANICIDE AGENTS

(75) Inventors: Nubia Boechat, Rio de Janeiro (BR); Marilia dos Santos Costa, Rio de Janeiro (BR); Maria Cristina da Silva Lourenço, Rio de Janeiro (BR); Ivan Neves, Jr., Rio de Janeiro (BR); Marcelo da Silva Genestra, Rio de Janeiro (BR); Vitor Francisco Ferreira, Rio de Janeiro (BR)

(73) Assignee: Fundacão Oswaldo Cruz—FIOCRUZ, Rio de Janeiro (BR)

( * ) Notice: Subject to any disclaimer, the term of this patent is extended or adjusted under 35 U.S.C. 154(b) by 0 days.

(21) Appl. No.: 12/981,315

(22) Filed: Dec. 29, 2010

(65) Prior Publication Data

US 2011/0269803 A1 Nov. 3, 2011

Related U.S. Application Data

(63) Continuation of application No. 12/064,241, filed on Jun. 16, 2008, now abandoned.

(30) Foreign Application Priority Data

Aug. 19, 2005 (BR) ...................................... 0503681

(51) Int. Cl.
*A61K 31/41* (2006.01)
*C07D 249/00* (2006.01)
(52) U.S. Cl.
USPC ......... 514/359; 514/398; 548/255; 548/326.5
(58) Field of Classification Search .................. 514/359, 514/398; 548/255, 326.5
See application file for complete search history.

(56) References Cited

U.S. PATENT DOCUMENTS

2005/0261333 A1  11/2005  Johansson et al.

OTHER PUBLICATIONS

Peter Scheiner, Tetrahedron, 1968, vol. 24(1), pp. 349-356.*
Arnold et al. "Synthetic Reactions of Dimethylformamide. XXVII. A Simple Synthesis of Aminomalonaldehyde Derivatives," *Collection Czechoslov. Chem. Commun.*, 38: 2633-2640, 1973.
Arnold et al., "Synthetic Reactions of Dimethylformamide. XXVIII. Diazomalonaldehyde," *Collection Czechoslov. Chem. Commun.*, 38: 2641-2647, 1973.
Croft et al. "Leishmaniasis- current chemotherapy and recent advances in the search for novel drugs," *TRENDS in Parasitology*, 19(11): 502-508, 2003.
El Khadem et al., "Synthesis of Triazole Derivatives of Sugars by 1,3 Dipolar Cycloaddition Addition From Acetylenic and Azido Precursors," *Carbohydrate Research*, 16(2): 209-218, 1971.
Huttel, Rudolf, Berichte der Deutschen Chemischen Gesellschaft [Abteilung] B: Abhandlungen, 74B, 1680-7, 1941.
Jakobsen et al. "Inhibitors of the Tissue Factor/Factor VIIa-Induced Coagulation: Synthesis and In Vitro Evaluation of Novel 2-Aryl Substituted Pyrido[3,4-d][1,3]-, Pyrido[2,3-d][1,3], Pyrazino[2,3-d][1,3]-,Pyrimido[4,5-d][1,3]-, Pyrazolo[3,4-d][1,3]-, Thieno[3,2-d][1,3]- and Thieno[2,3-d][1,3]-oxazin-4-ones," *Bioorg. Med. Chem.*, 8: 2803-2812, 2000.
L'abbe, et al., "Molecular Rearrangements of 4-Iminomethyl-1,2,3-Triazoles Replacement of I-Aryl Substituents in 1-*H*-1,2,3-Triazole-4-carbaldehydes," *J. Het. Chem*, 27(7): 2021-2027, 1990.
Rossetti et al. "Resistant tuberculosis: a molecular review," *Rev Saúde Pública*, 36(4): 525-532, 2002.
Sheehan et al., "The Synthesis of Phenyl-substituted Triazole Analogs of Histamine," *JACS*, 73: 1207-1210,esp. p. 1209, 1951.
Tripathi et al. "Fighting Tuberculosis: An Old Disease with New Challenges," *Med. Res.Rev.*, 25(1): 93-131, 2005.
Wamhoff et al. "Heterocyclische β-Enaminoester; 55. Imidazo[4,5-d], Thiazolo[5,4-d]- and Thiazolo[4,5-*d*,][1,3]oxazinone," *Synthesis*, 1993(1): 107-111,1993.

* cited by examiner

*Primary Examiner* — Susannah Chung
(74) *Attorney, Agent, or Firm* — Klarquist Sparkman, LLP

(57) ABSTRACT

This invention refers to new 1,2,3-triazole and imidazole compounds included in the families of compounds represented by general formula VIII. This invention also refers to a pharmaceutical composition comprising at least one of the azole compounds represented by the general formula VIII, to the use of such compositions and to methods of treatment or inhibition of tuberculosis and leishmaniasis.

9 Claims, 4 Drawing Sheets

AZOLE COMPOUNDS USED AS TUBERCULOSTATIC AND LEISHMANICIDE AGENTS

This invention refers to azole compounds pertaining to the 1,2,3-triazole and imidazole classes that can be used to treat tuberculosis and leishmaniasis, with the advantage of having high activity against microorganisms, more specifically against *Mycobacterium tuberculosis* and protozoa of *Leishmania* gender, agents that cause these diseases, as well as their salts, its stereoisomeric forms, racemic mixtures, prodrugs, their metabolites; as well as pharmacological compositions containing at least one of these compounds or their salt as an active principle and to the use of such compositions as drugs to treat or inhibit diseases.

Besides that, this invention also includes a treatment method or inhibition of tuberculosis and leishmaniasis, with the advantage of presenting a high activity against microorganisms, more specifically against *Mycobacterium tuberculosis* and protozoa of the *Leishmania* gender, comprising the administration of a pharmacologically effective quantity of at least one of these compounds or their salt, to the living being that needs the referred treatment or inhibition.

BACKGROUND OF INVENTION

Millions of persons in the world continue to die of diseases that can be treated, prevented or even inhibited. Inadequate or even non-existing treatments to infectious and parasitic diseases are victimizing an elevated number or persons, especially in countries in development. Thousands of lives are lost or severely damaged due to these diseases that impact the social well-being and exclude an important parcel of individuals from their social and productivity activities.

Neglected diseases is the classification attributed to diseases that do not present a satisfactory treatment, do not create interest in pharmaceutical industries and, besides that, government funding is insufficient to fight these kinds of diseases. Tuberculosis, HIV/Aids and malaria are examples of neglected diseases, because although they affect individuals from developed countries, they mainly afflict populations of countries in development and they create only a peripheral interest from the pharmaceutical market. The lack of investment from pharmaceutical industries in the development of new drugs for certain diseases is directly connected to the low capacity of purchase of populations of countries in development.

The lack of interest, on the part of the pharmaceutical industries, for neglected diseases is so severe that within the period of 25 years, from 1975 to 1999, from the 1.393 new drugs licensed, only 15 pertain to this class, 13 being for tropical diseases and 2 for tuberculosis.

The urgency on the discovery of new drugs for neglected and extremely neglected diseases has motivated survey and development in several countries, including Brazil.

Tuberculosis (TB) is an infectious disease transmitted through the airway by a bacterium called *Mycobacterium tuberculosis*, also known as Koch *bacillus* in honor of the scientist Robert Koch, who isolated it in 1882. There are several forms of tuberculosis (lung, meningeal, milliary, bone, renal, cutaneous, genital, etc), however, the most frequent form and the most contagious one is the pulmonary. A patient with pulmonary tuberculosis, if not treated, can infect from 10 to 15 persons in a year.

From reports of the presence of fragments of the *bacillus* in Egyptian mummies in 2400 B.C., tuberculosis presently infects approximately one third of the world population and it is the main cause of death in countries in development. We estimate that 70% of the population in destitute countries is infected by the Koch *bacillus*, and every year, 7.5 million new cases are reported and 2.8 million of deaths. The high rate of incidence of the disease in these is closely connected to the precarious life conditions of the population. In India, for instance, which holds 15% of global populations, approximately 30% of the population is infected by the *M. tuberculosis* and tuberculosis kills 14 times more people than all tropical diseases.

Brazil, according to the World Health Organization (WHO), presents the most elevated number of cases of tuberculosis in Latin America, that is, 62 new cases per 100.000 inhabitants, presently being the fourteenth among the 23 countries responsible for 80% of the total cases of tuberculosis in the world. Sources from Health Ministry estimate a prevalence of 58/100.000 cases/inhabitants, within the country, with approximately 111 mil new cases/year, and Rio de Janeiro being the state with higher incidence and occurrence of approximately e 6.0 mil deaths/year from the disease.

HIV infection is one of the most significant risk factors known for tuberculosis infection.

It is estimated that one third of 42 million individuals infected by HIV are co-infected by *M. tuberculosis* and most of the persons infected by HIV develop TB as their first AIDS sign. Since HIV progressively destroys the immune system, there is a greater chance that virus infected persons develop tuberculosis. This relation among epidemics is especially concentrated in destitute countries. In Sub-Saharian Africa, for instance, approximately 50% of persons with HIV develop TB and one in three dies in consequence of the disease.

On the other hand, the increased number of multidrug-resistant tuberculosis (TBMR) has caused great concern, because it contributes to increase the ration of deaths by TB, and being frequently associated to HIV infection.

Tuberculosis is a serious disease, but it is curable in practically 100% of new cases, as long as modern chemotherapy principles are followed, the adequate association of drugs and their regular use, for sufficient time are the necessary means to avoid bacterial resistance and persistence.

Chemotherapy for tuberculosis started during the 40's when the studies about tuberculostatic agents resulted in the discovery of several active substances face *M. tuberculosis* (Tripathi, R. P.; Tewari, N.; Dwivedi, N.; Tiwari, V. K.; "Fighting Tuberculosis: An Old Disease with New Challenges"; Med. Res. Rev., 2005, 25, 1, 93-131). The presence of multi-resistant lineages reflects deficiencies in the control of TB, thus hindering treatment and prevention of the disease, causing its propagation (Rossetti, M. L. R.; Valim, A. R. M.; Silva, M. S. N.; Rodrigues, V. S.; "Tuberculosis resistente: revisdo molecular"; Rev. Saúde Pública, 2002, 36, 525-32).

The first drug really active against tuberculosis, discovered by Selman Walksman, in 1943, was streptomycin (SM) (Formula I where R=CHO) an aminoglycoside antibiotic insulated from the *Streptomyces griseus* bacterium. However, SM administered in higher doses can affect the central and peripheral nervous systems. Different synthetic by products from streptomycin have been synthesized and have shown to be active as tuberculostatic, such as, for example, dihydrostreptomycin (Formula I where R=$CH_2OH$), which although demonstrates to be active can cause irreversible damage to the hearing system.

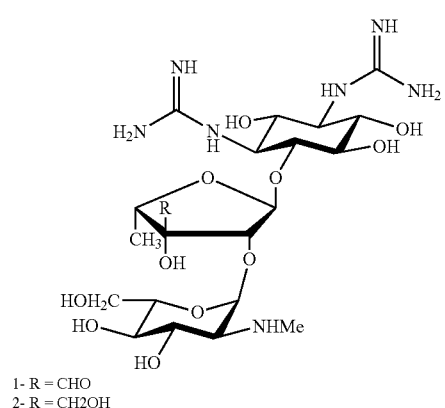

1- R = CHO
2- R = CH2OH

The p-amino-salicylic acid (PAS) (Formula II), first reported in 1946, presents great and selective activity against *M. tuberculosis*. It was used combined to SM, but presently, according to WHO, its use is directed to the multidrug-resistant tuberculosis treatment.

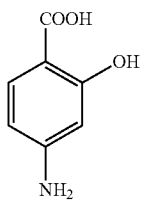

(II)

With progress of researches, new drugs have been introduced in therapy. Some of them are still used in treating tuberculosis, such isoniazide (INH) (Formula III), firstly used in 1952, and rifampicin (RMP) (Formula IV), used as of 1967. These medicaments are still the basis of modern chemotherapy in treating the disease.

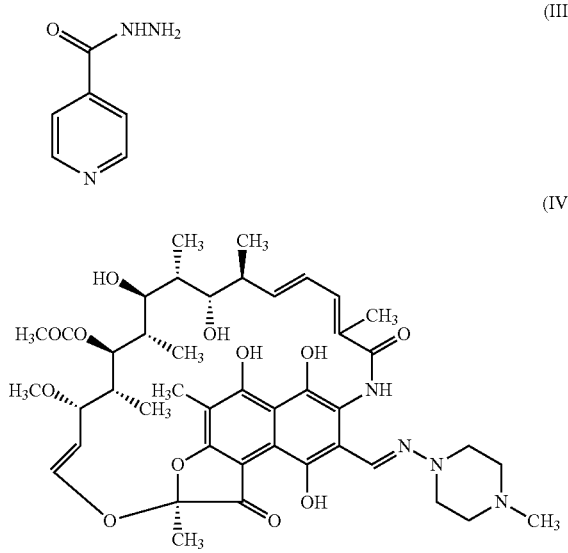

INH (Formula III) is active orally and besides exhibiting a bacteriostatic action against the *bacillus*, it is highly active against the *M. avium* complex. Its minimum inhibitory concentration (MIC) is very low (0.02-0.06 µg/mL) fact that contributes to its efficacy.

On the other hand, rifampicin (Formula IV, which is part of a semi-synthetic antibiotics group derived from rifamicin B, insulated from *Streptomyces mediterrani*, is extremely effective against *M. tuberculosis*, with a MIC of 0.1 µg/mL to 1.0 µg/mL, and it presents a quick bactericide action in the elimination of persistent bacteria.

Due to its efficacy and ease administration, rifampicin (Formula IV) is the drug chosen to treat patients co-infected by TB/HIV. However, rifampicin, as other by products of this class, presents a significant pharmaceutical interaction with several of the anti-retroviral, especially with protease inhibitors that have their concentration decreased by the inducing action of rifampicin.

Several compounds similar to INH have been synthesized and some have shown activity against *M. tuberculosis* H37Rv. Among them ethionamide (Formula V) and a pyrazinamide (PZA) (Formula VI), which are also used in TB chemotherapy.

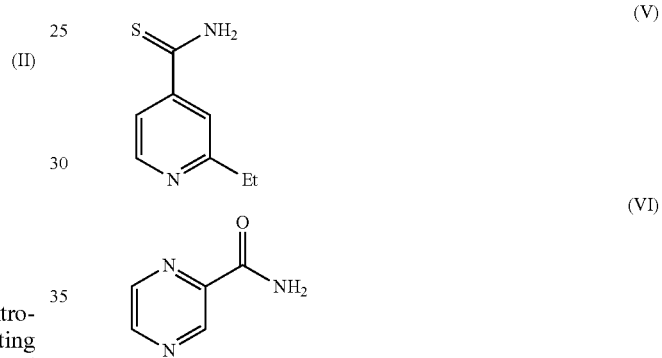

Other significant drug used in treating tuberculosis, since 1968, is ethambutol (EMB) (Figure VII) which is active against many variables of *Mycobacterium*. EMB is a synthetic amino alcohol, firstly synthesized in 1960, with enantiomer as its stereo specific activity (Figure VII) with S,S configuration is the isomer that shows a tuberculostatic action, as the enantiomer R,R presents an undesirable action, since it causes blindness.

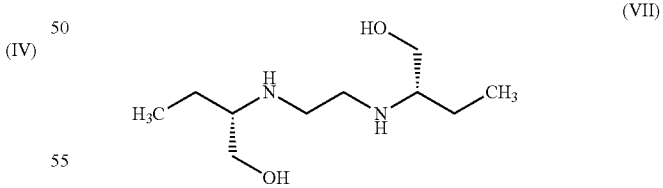

Drugs used in the tuberculosis can be classified as first line and second line drugs. First line drugs are part of the TB primary treatment plan and consist of the four medications previously mentioned isoniazide, rifampicin, pyrazinamide and ethambutol. The adequate treatment of patients with combinations of these agents during long periods (six to nine months) leads to cure in 95% of TB cases.

However, in cases with monotherapy, inadequate prescription, incorrect use of the primary plan by the patient or even intolerance to first line drugs can lead to failure in therapy and development of the *M. tuberculosis* strains resistant to one or more drugs. In this case, second line drugs are used.

Along with streptomycin (SM), p-amino salicylic acid and ethionamide, drugs used in the second chemotherapy plan are: Thiacetazone, D-cycloserine, clofazimine, terizidone, kanamycin and amicacin.

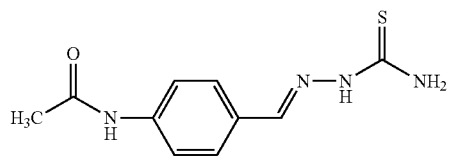

Tiacetozona

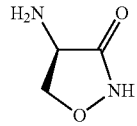

D-Cicloserina

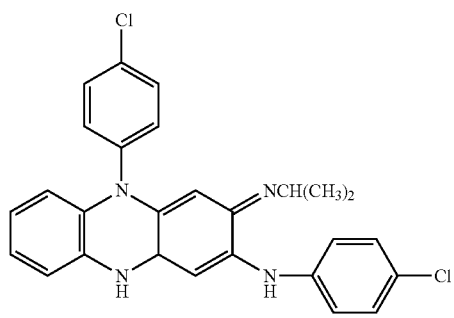

Clorofazimina

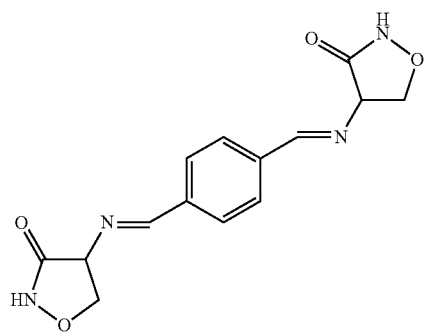

Terizidona

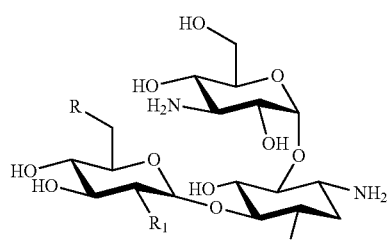

Canamicina

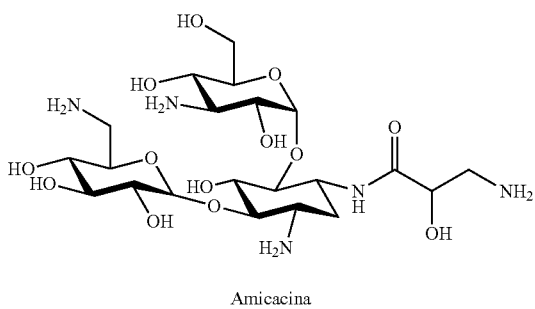

Amicacina

A - R = $NH_2$ $R_1$ = OH
B - R = $R_1$ = $NH_2$
C - R = OH $R_1$ = $NH_2$
(Translation- Thiacetazone, D-Cycloserine, clofazimine, terizidone, kanamycin, amicacin.)

A significant class of antibiotics, fluoroquinolones, has been used in pulmonary, extrapulmonary and disseminated tuberculosis. These compounds were approved by WHO as second line agents to TBMR treatment and are employed in cases of resistance or intolerance to first line drugs.

Clinical studies have shown that during the first 48 hours of pulmonary tuberculosis ciprofloxacin and ofloxacin have demonstrated to be less potent than isoniazide. However, a gatifloxacin and moxifloxacin have shown a greater activity in relation to INH. A fact that should be mentioned is the non-existence of toxicity in ten patients submitted to six months therapy with moxifloxacin, isoniazide and rifampicin. Due to the high activity of the fluoroquinones as bactericides, several clinical studies are being made in order to make them first line drugs.

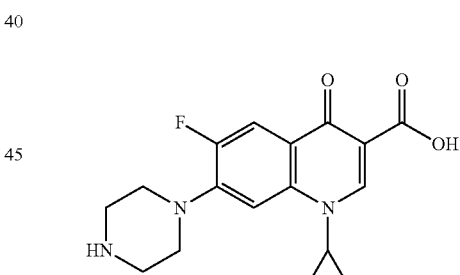

Ciprofloxacina
MIC = 0,5-4,0 μg/mL

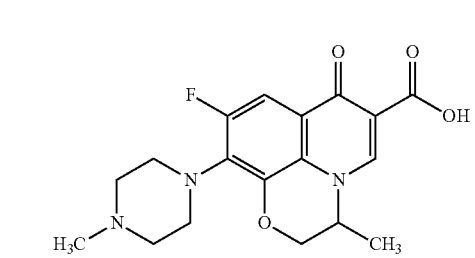

Ofloxacina
MIC = 1,5-2,0 μg/mL

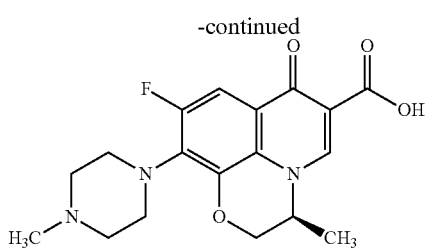

Levofloxacina
MIC = 1,5-2,0 μg/mL

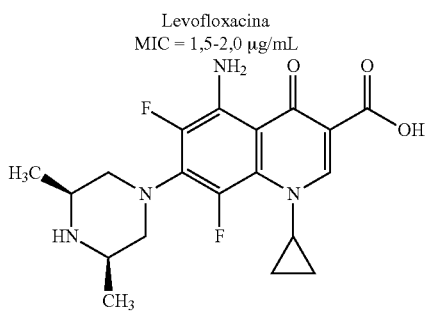

Esparfloxacina
MIC = 0,2-0,5 μg/mL

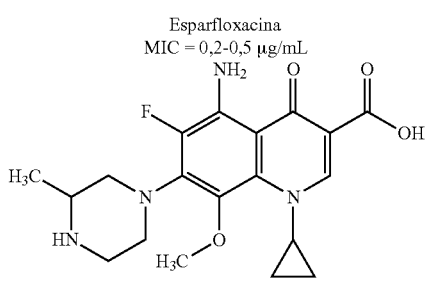

Gatifloxacina
MIC = 0,2-0,25 μg/mL

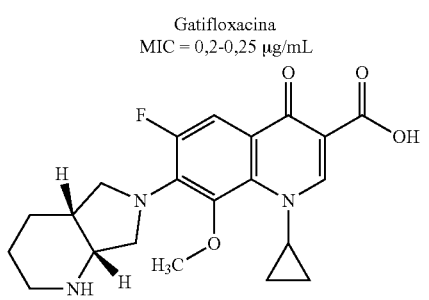

Moxifloxacina
MIC = 0,12-0,5 μg/mL

Leishmaniasis depicts a complex of diseases with a significant clinical and epidemiological diversity. Caused by approximately 20 species of protozoa of the *Leishmania* gender, it is transmitted to men by the sting of the female mosquito of the *Phebotomine* species in Europe and of the *Lutzomyia* species in South and Central America.

The diseases present two clinical forms: integumental leishmaniasis and visceral leishmaniasis. The Cutaneous Leishmaniasis (LC) is the most common of the manifestations and it is characterized by ulcerative nodular lesions. The onset of lesions appears where the vector insect stung, thus being more frequent in body areas exposed, for instance, limbs and face. The incubation period between the sting and the onset of the lesion can vary from a few weeks to months. However, the cutaneous leishmaniasis disseminated (LCD) is characterized by multiple and small lesions, with or without central ulceration, sometimes with an acneiform aspect. The diffuse form is a rare form of the disease detected in some of the Brazilian states, such as Maranhao, Para, Bahia and Mato Grosso.

The drugs presently recommended for the treatment of leishmaniasis (Croft, S. L.; Coombs, G. H.; "Leishmaniasis—current chemotherapy and recent advances in the search for novel drugs" Trends Parasit., 2003, 19, 502-508) are the pentavalent—the sodium stibogluconate (Pentostam®), the meglumine antimoniate(Glucantime®), the pentamidine and the amphotericin B and its three lipidic formulations—a liposomal amphotericin B, colloidal dispersion amphotericin B and a lipidic complex amphotericin B. Pentamidine was introduced in 1952 in therapy and even today it used as a third choice drug. Its use as a leishmanicide agent is restricted due to its high toxicity that can cause adverse effects such as nausea, vomiting, headache, hypoglycemia and sudden death.

Due to increased cases of leishmaniasis and to long and inadequate treatments with toxic drugs that are hard to be administered, the discovery of new leishmanicide agents has become mandatory.

There is not, in all the extension of chemical, pharmacological and medical literature, either in magazines, journals, encyclopedias, books or patents, a quotation for the use of the 1,2,3-triazoles and imidazole as tuberculostatic and leishmanicide agents, of potential use for the treatment of tuberculosis and leishmaniasis.

ABSTRACT OF THE INVENTION

Considering the need to manufacture new drugs to treat and inhibit tuberculosis and leishmaniasis new compounds 1,2,3-triazole and imidazole composed were developed, included in the family of the compounds represented by the general formula VIII.

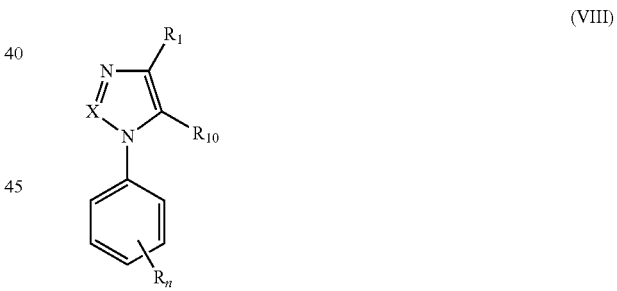

(VIII)

where:
X is an atom of "C" or "N"
when X is "N" radicals of the triazole ring are represented by:
$R_1$=COR$_2$, CSR$_3$, CN(R$_4$)R$_5$ or CF$_2$R$_6$;
$R_2$=H, NHNH$_2$, alkyl, aryl substituted or not, OH, NR$_7$R$_8$ or OR$_9$
$R_3$=alkyl or aryl substitute or not
$R_4$=H, OH, alkyl or aryl substituted or not
$R_5$=R$_6$=R$_7$=R$_8$=R$_9$=R$_{10}$=H, alkyl or aryl substituted or not
when X is "C" radicals of the imidazole ring are represented by:
$R_1$=COR$_2$
$R_2$=NHNH$_2$, OH, OR$_3$, or NR$_4$R$_5$
$R_3$=alkyl or aryl substituted or not
$R_4$=R$_5$=H, alkyl or aryl substituted or not
$R_{10}$=NHR$_6$ or NR$_6$R$_7$
$R_6$=R$_7$=COR$_8$ $R_8$=aryl substituted or not while radical $R_n$ can be located in any one or in more than one of the carbon atoms of the aromatic ring, and these radicals can be equal or different, represented by hydrogen, alkylic groups with 1 or more carbon atoms in a linear or branched chain alkenes or alkynes, hydroxyl, hydroxyalkyl or oxygenated functions in acyclic or cyclic systems forming an heterocyclic ring, free or substituted amines, thioalkyl, donators and/or removing groupings of electrons or halogens, thus "n" can vary from 1 to 5.

Another objective of this invention refers to the pharmaceutical composition comprising, as active principle, at least one of the 1,2,3-triazole and/or imidazole compounds represented by the general formula VIII.

Another objective of this invention is related to the use of such compositions as drugs to treat or inhibit tuberculosis and leishmaniasis.

Another objective of this invention refers to a method for treating or inhibiting tuberculosis and leishmaniasis.

The compounds 1,2,3-triazole and imidazole of formula VIII can be under the form of salts, stereoisomeric forms, racemic mixtures, pro-drugs and metabolites, and can be used as tuberculostatic and leishmanicide agents, to treat tuberculosis and leishmaniasis, with the advantage of presenting high activity against microorganisms.

DETAILED DESCRIPTION OF THE INVENTION

This invention refers to the new 1,2,3-triazole and imidazole compounds included in the family of compounds represented by general formula VIII

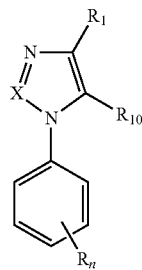

(VIII)

where:
X is an atom of "C" or "N"
when X is "N" the radicals of the triazole ring is represented by:
$R_1$=$COR_2$, $CSR_3$, $CN(R_4)R_5$ or $CF_2R_6$;
$R_2$=H, $NHNH_2$, alkyl, aryl substituted or not, OH, $NR_7R_8$ or $OR_9$
$R_3$=alkyl or aryl substituted or not
$R_4$=H, OH, alkyl or aryl substituted or not
$R_5$=$R_6$=$R_7$=$R_8$=$R_9$=$R_{10}$=H, alkyl or aryl substituted or not
when X is "C" the radicals of the imidazole ring are represented by:
$R_1$=$COR_2$
$R_2$=$NHNH_2$, OH, $OR_3$, or $NR_4R_5$
$R_3$=alkyl or aryl substituted or not
$R_4$=$R_5$=H, alkyl or aryl substituted or not
$R_{10}$=$NHR_6$ or $NR_6R_7$
$R_6$=$R_7$=$COR_8$
$R_8$=aryl substituted or not
while radical $R_n$ can be located in any one or in more than one of the carbon atoms of the aromatic ring, and these radicals can be equal or different, represented by hydrogen, alkylic groups with 1 or more carbon atoms in a linear or branched chain alkenes or alkynes, hydroxyl, hydroxyalkyl or oxygenated functions in acyclic or cyclic systems forming an heterocyclic ring, free or substituted amines, thioalkyl, donators and/or removing groupings of electrons or halogens, thus "n" can vary from 1 to 5.

In this invention all the compounds are presented as freebase or pharmaceutically accepted salts of them, preferably chlorides.

More particularly, compounds 1,2,3-triazole can be selected among:
4-carboxaldehyde-1-(4-chlorophenyl)-1H-1,2,3-triazole;
4-carboxaldehyde-1-(4-bromophenyl)-1H-1,2,3-triazole;
4-carboxaldehyde-1-(4-methylphenyl)-1H-1,2,3-triazole;
4-carboxaldehyde-1-(4-methoxyphenyl)-1H-1,2,3-triazole;
4-carboxaldehyde-1-(2,5-dimethoxyphenyl)-1H-1,2,3-triazole;
4-carboxaldehyde-1-(3-chlorophenyl)-1H-1,2,3-triazole;
4-carboxaldehyde-1-(3,5-dichlorophenyl)-1H-1,2,3-triazole;
4-carboxaldehyde-1-(3-cyanophenyl)-1H-1,2,3-triazole;
4-carboxaldehyde-1-(4-cyanophenyl)-1H-1,2,3-triazole;
4-carboxaldehyde-1-(4-nitrophenyl)-1H-1,2,3-triazole;
4-carboxaldehyde-1-(2-methoxyphenyl)-1H-1,2,3-triazole;
4-carboxaldehyde-1-(3,4-dimethoxyphenyl)-1H-1,2,3-triazole;
1-(4-chlorophenyl)-4-difluoromethyl-1H-1,2,3-triazole;
1-(4-bromophenyl)-4-difluoromethyl-1H-1,2,3-triazole;
1-(4-methylphenyl)-4-difluoromethyl-1H-1,2,3-triazole;
1-(4-methoxyphenyl)-4-difluoromethyl-1H-1,2,3-triazole;
1-(2,5-dimethoxyphenyl)-4-difluoromethyl-1H-1,2,3-triazole;
1-(3-chlorophenyl)-4-difluoromethyl-1H-1,2,3-triazole;
1-(3,5-dichlorophenyl)-4-difluoromethyl-1H-1,2,3-triazole;
1-(3-cyanophenyl)-4-difluoromethyl-1H-1,2,3-triazole;
1-(4-cyanophenyl)-4-difluoromethyl-1H-1,2,3-triazole;
1-(4-nitrophenyl)-4-difluoromethyl-1H-1,2,3-triazole;
1-(2-methoxyphenyl)-4-difluoromethyl-1H-1,2,3-triazole;
1-(3,4-dimethoxyphenyl)-4-difluoromethyl-1H-1,2,3-triazole;
(AND)-4-chloride-N-((1-(4-chlorophenyl)-1H-1,2,3-triazole-4-il)methylene)benzenamine; and,
(E)-4-bromo-N-((1-(4-bromophenyl)-1H-1,2,3-triazole-4-il) methylene)benzenamine
which are 1,2,3-triazole compounds or a pharmaceutical accepted salt of it, preferably chloride, combined with a pharmaceutically acceptable vehicle.

Compounds 1,2,3-triazole presented in this invention can be synthesized according to processes known by experts in this area, as described in articles "Arnold, Z.; Šauliová, J.; Krchňák, V.; *Synthetic Reactions of Dimethylformamide. XXVII. A Simple Synthesis of Aminomalonaldehyde Derivatives*, Coll. Czec. Chem. Commun., 1973, 38, 2633-2640"; and, "Arnold, Z.; Šauliová, J.; Synthetic Reactions of Dimethylformamide. XXVIII. Diazomalonaldehyde; Coll. Czec. Chem. Commun., 1973, 38, 2641-2647", but always observing the balance of their intrinsic lipophilic and hydrophilic characteristics, because it influences the antimicrobial leishmanicide activity.

With reference to imidazole compounds they can be preferably selected among:
Ester 5-[(bis(4-fluorobenzoic)amino]-1-(4-methylphenyl)-1H-imidazole-4-carboxylate of ethyl;
Ethyl Ester 5-[(bis(4-fluorobenzoic)amino]-1-(4-cyanophenyl)-1H-imidazole-4-carboxylate;

Ethyl Ester 5-[(bis(4-fluorobenzoic)amino]-1-(4-chlorophe-nyl)-1H-imidazole-4-carboxylate;
Ethyl Ester 5-[(bis(4-fluorobenzoic)amino]-1-(3,5-dichlo-ridephe-nyl)-1H-imidazole-4-carboxylate;
Ethyl Ester 5-[(bis(4-fluorobenzoic)amino]-1-(2,6-difluo-rophe-nyl)-1H-imidazole-4-carboxylate;
Ethyl Ester 5-[(bis(2-fluorobenzoic)amino]-1-(4-methylphe-nyl)-1H-imidazole-4-carboxylate;
Ethyl Ester 5-[(bis(2-fluorobenzoic)amino]-1-(4-cyanophe-nyl)-1H-imidazole-4-carboxylate;
Ethyl Ester 5-[(bis(2-fluorobenzoic)amino]-1-(4-chlorophe-nyl)-1H-imidazole-4-carboxylate;
Ethyl Ester 5-[(bis(2-fluorobenzoic)amino]-1-(3,5-dichlo-ridephe-nyl)-1H-imidazole-4-carboxylate;
Ethyl 5-[(bis(2-fluorobenzoic)amino]-1-(2,6-difluorophe-nyl)-1H-imidazole-4-carboxylate;
Ethyl Ester 5-[(4-fluorobenzoic)amino]-1-(4-methylphe-nyl)-1H-imidazole-4-carboxylate;
Ethyl Ester 1-(4-cyanophenyl)-5-[(4-fluorobenzoic)amino]-1H-imidazole-4-carboxylate;
Ethyl Ester 1-(4-chlorophenyl)-5-[(4-fluorobenzoic)amino]-1H-imidazole-4-carboxylate;
Ethyl Ester 1-(3,5-dichlorophenyl)-5-[(4-fluorobenzoic)amino]-1H-imidazole-4-carboxylate;
Ethyl ester 1-(2,6-difluorophenyl)-5-[(4-fluorobenzoic)amino]-1H-imidazole-4-carboxylate;
Ethyl Ester 5-[(2-fluorobenzoic)amino]-1-(4-methylphe-nyl)-1H-imidazole-4-carboxylate;
Ethyl Ester 1-(4-cyanophenyl)-5-[(2-fluorobenzoic)amino]-1H-imidazole-4-carboxylate;
Ethyl Ester 1-(4-chlorophenyl)-5-[(2-fluorobenzoic)amino]-1H-imidazole-4-carboxylate;
Ethyl Ester 1-(3,5-dichlorophenyl)-5-[(2-fluorobenzoic)amino]-1H-imidazole-4-carboxylate; and,
Ethyl Ester 1-(2,6-difluorophenyl)-5-[(2-fluorobenzoic)amino]-1H-imidazole-4-carboxylate.

Imidazole compounds presented in this invention can be synthesized according to processes known by experts in this area, as described in articles "Wamhoff, H.; Berressem, R.; Herrmann, S.; *Heterocyclishe β-Enaminoester;* 55. Imidazo[4,5-d]-, Thiazolo[5,4-d]-und Thiazolo[4,5-d][1,3] oxazi-none; Synthesis, 1993, 107-111" and "Jakobsen, Palle; Horneman, A. M.; Persson, AND.; *Inhibitors of the Tissue Factor/Factor VIIa-Induced Coagulation: Synthesis and In Vitro Evaluation of Novel* 2-Aryl-Substituted Pyrido[3,4-d][1,3]-, Pyrido[2,3-d][1,3]-, Pyrazino[2,3-d][1,3]-, Pyrimido[4,5-d][1,3], Pyrazolo[4,5-d][1,3]-, Thieno[2,3-d][1,3]-, and Thieno[2,3-d][1,3]-,oxazin-4-ones; *Bioorg. Med. Chem.;* 2000, 8, 2803-2812" but always observing the balance of their intrinsic lipophilic and hydrophilic characteristics, because it influences the antimicrobial and leishmanicide activity.

Pharmaceutical compounds containing at least one 1,2,3-triazole and/or imidazole compounds of this invention, or a salt of it, can be administered in the pharmaceutical form of solution, suspension, emulsion, ointment, cream, gel, tablet or capsule, oral, injection or topic use, prepared as of powder, solution or suspension of at least one of the compounds in an adequate concentration, and in a vehicle pharmaceutically acceptable, in order to create the adequate dosage form. These compositions are employed in the treatment or inhibition of tuberculosis and leishmaniasis.

BRIEF DESCRIPTION OF FIGURES

In order to enable a better understanding of the invention, below, we have listed the figures with a brief description of them.

In Figures, compounds were represented by codes, and the correlation among them is listed on Table 1:

TABLE 1

Correlation among compounds and codes

| Compounds | Code |
|---|---|
| 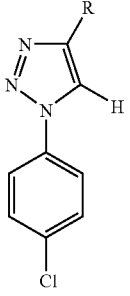 R = CHO | 114a |
| 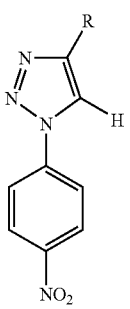 R = CHO | 114j |
| 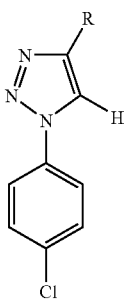 R = CHF$_2$ | 121a |
| 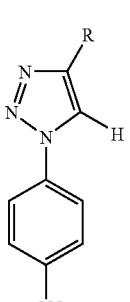 R = CHF$_2$ | 121j |

Figure 1:
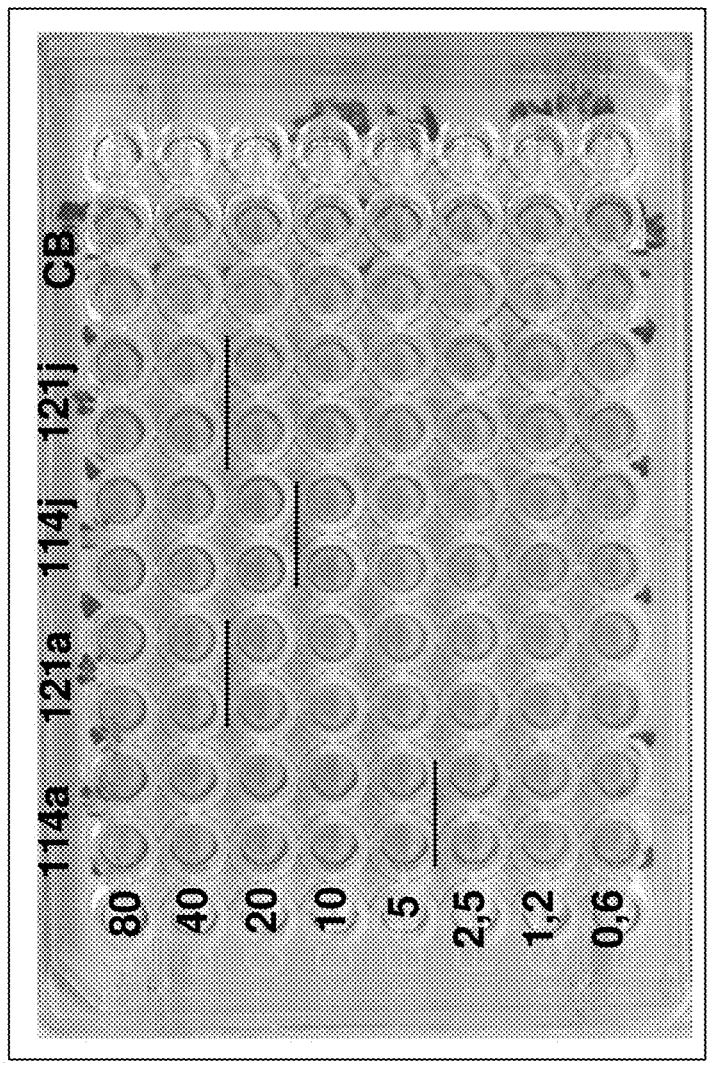
Figure 2:
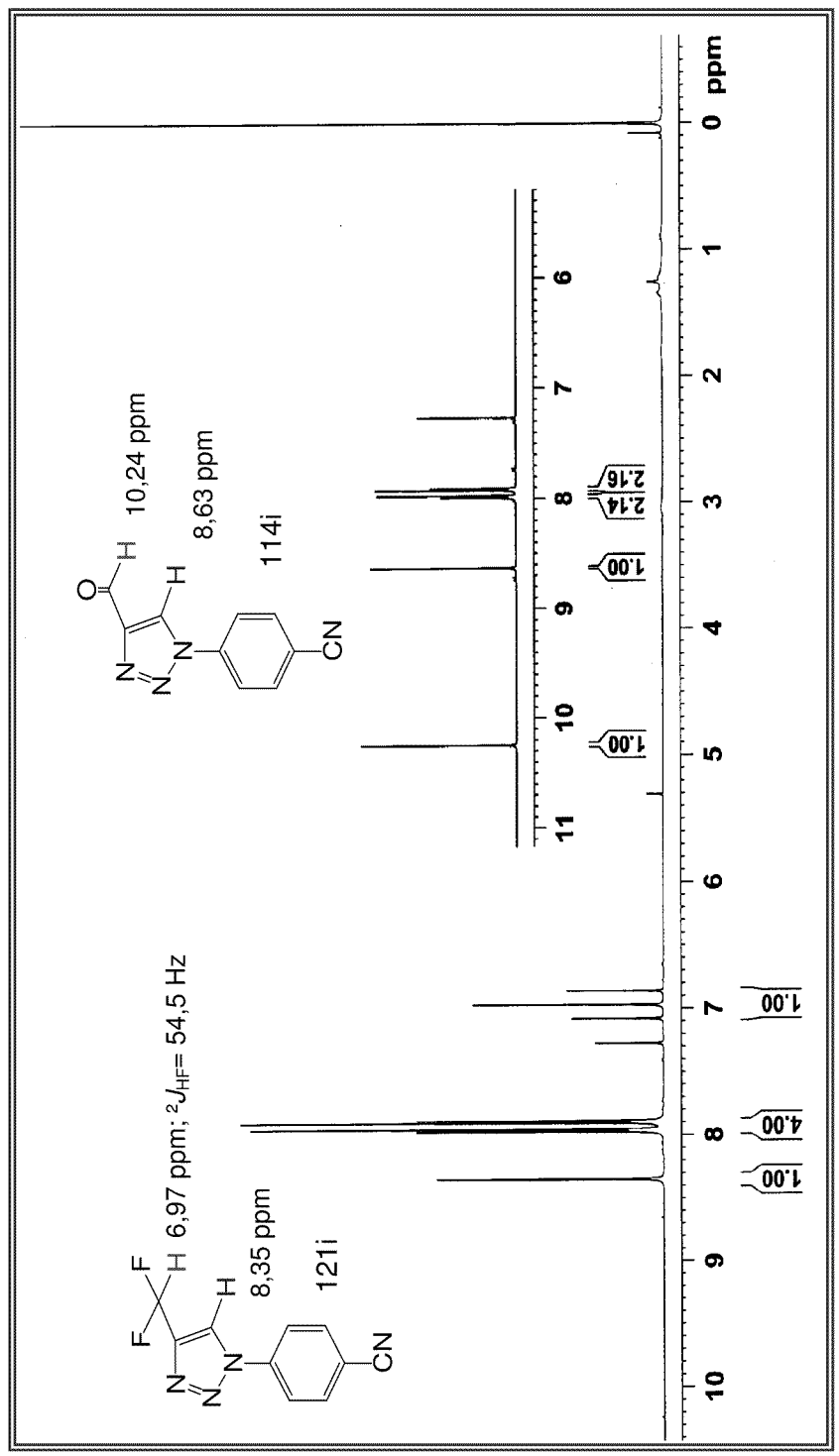

FIG. 1—Essay of antimicrobial activity of compounds 1,2,3-triazole type I and II FIG. 2—Spectrum of proton RMN of derivatives 1,2,3-triazole 114i (type I) and 121i (type II).

Figure 3:
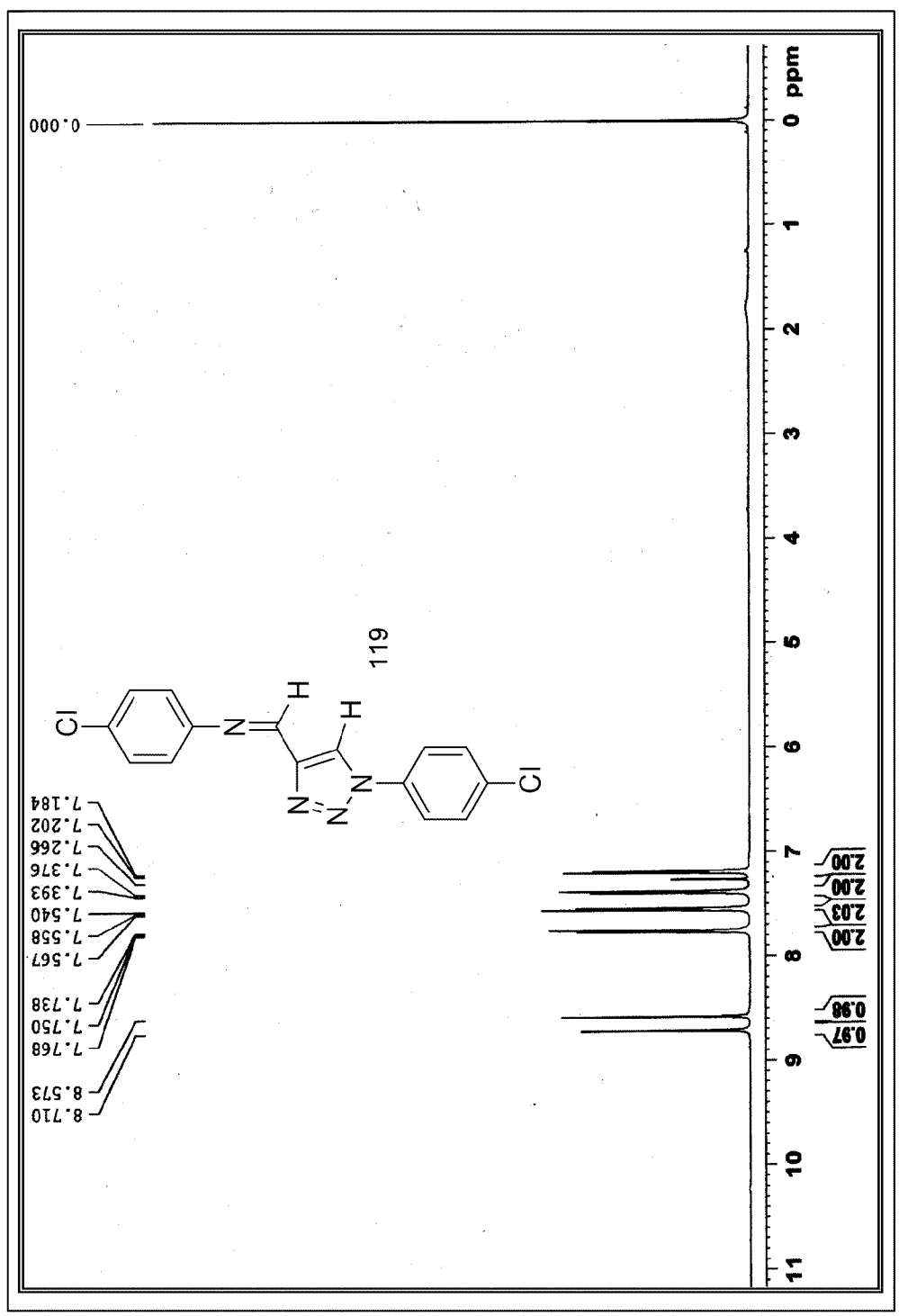

FIG. 3—Spectrum of proton RMN derivatives 1,2,3-triazole 119 (type III).

Figure 4:
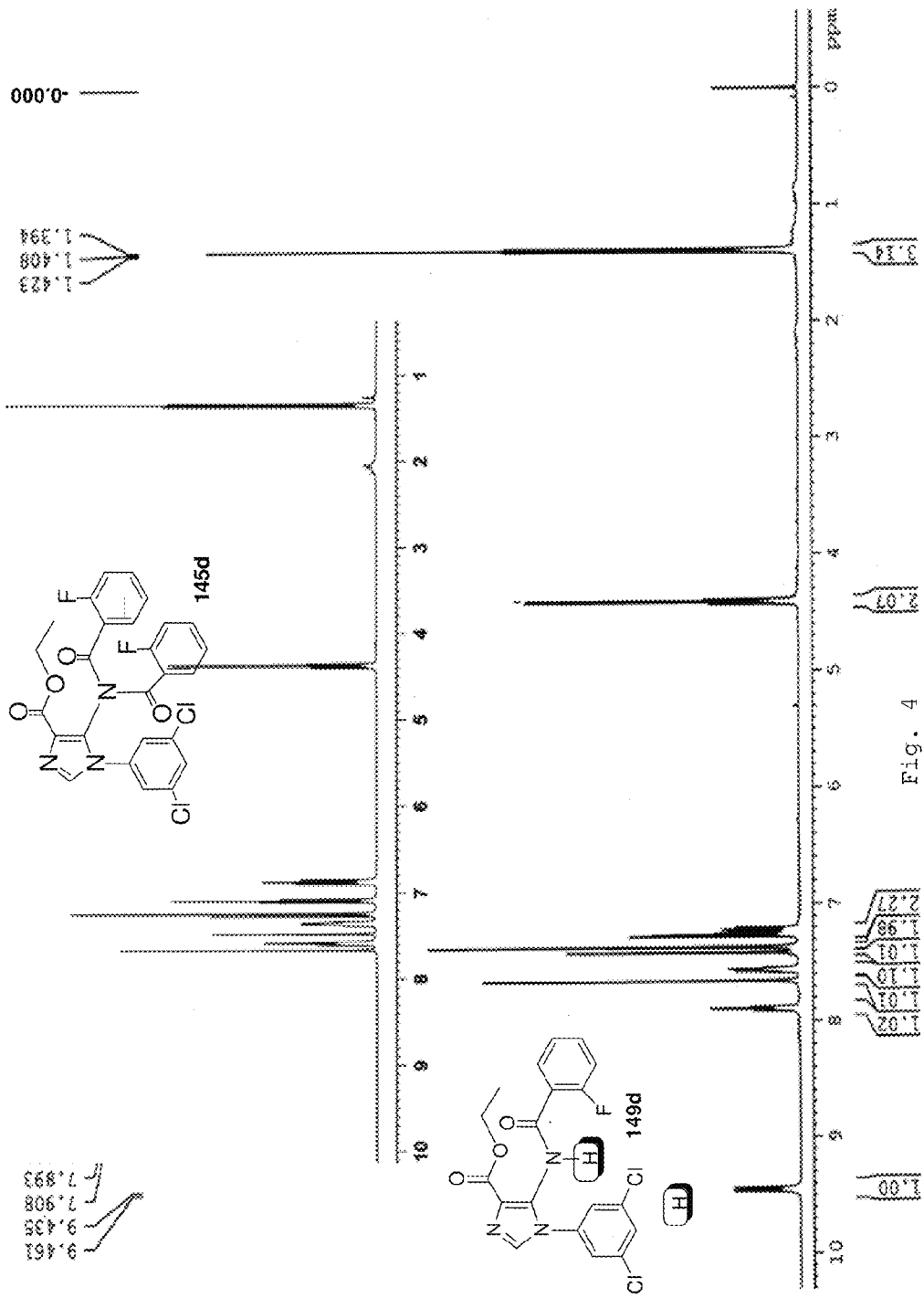

FIG. 4—Spectrum of proton RMN derivatives imidazole 145d (di-substituted) and 149d (mono-substituted).

DETAILED DESCRIPTION OF INVENTION

This invention is described in detail through examples presented as follows. It is necessary to emphasize that the invention is not limited to these examples, but it also includes several variations and modifications within the limits within which it acts.

EXAMPLE 1

A—Pharmacological evaluation of the triazole derivatives of type I (Formula IX) and II (Formula X)

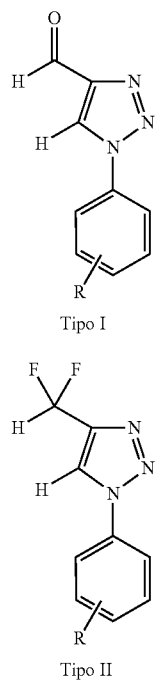

Tipo I

Tipo II

A.1—Antimicrobial Activity

Type I and II 1,2,3-triazole derivatives were submitted to a primary biological evaluation, in vitro, regarding the inhibitory activity of the *Mycobacterium tuberculosis* H37Rv (ATCC-27294).

The definition of minimum inhibitory concentrations (MIC) of substances, that is, the smallest concentration of the compound in which bacterial growth is not observed, was made using the colorimetric method known as MABA (Microplate Alamar Blue Assay). This method consists in an essay performed by the micro dilution in plates, using, as cell growth indicator, the Alamar Blue® indicator pigment, which is a fluorescent/colorimetric indicator with redox property. The oxidized form is blue (non-fluorescent) and indicates the absence of bacterial growth. The reduced form presents a pink color (fluorescent), indicates the proliferation of bacteria. This methodology has been applied to determine the resistance profile of microbacteria to antimicrobials (FIG. I).

To perform the essay, sterile micro plates with 96 wells were used in a way that each wells presented a total of 200 μL of a mixture composed by the adequate culture mean, of the compound to be tested and of the bacterial suspension. The comparison pattern used was rifampicin, which presents a MIC equal to 1.0 μg/mL.

After 5 incubation days, 15 μL of Alamar Blue® was added to each well and microplates were incubated for more than 24 hours at 37° C. At the end of this period of time, the change of color in each well was observed, and MIC was defined as the smallest concentration of the compound that delimitates the change from blue to pink.

Thus, the antimicrobial activity essay of compounds 114a, 121a, 114j and 121j was performed, observing that the same were able to inhibit bacterial growth. As can be seen in FIG. 1, compounds presented MIC of 5 μg/mL, 40 μg/mL, 20 μg/mL and 40 μg/mL, respectively.

The other compounds in this series were evaluated and Table 2 shows the values defined for MIC, in μg/mL, and the inhibition percentage presented by each substance.

TABLE 2

Antimicrobial activity of type I and II compounds against *M. tuberculosis* H37Rv (ATCC 27294) MIC Data and inhibition percentage

| R | Type I | MIC (μg/mL) | Inhibition (%) | Type II | MIC (μg/mL) | Inhibition (%) |
|---|---|---|---|---|---|---|
| 4-Cl | 114a | 5.0 | na* | 121a | 40.0 | nd |
| 4-Br | 114b | 5.0 | 100 | 121b | 20.0 | 75 |
| 4-CH$_3$ | 114c | 2.5 | 100 | 121c | 40.0 | 87 |
| 4-OCH$_3$ | 114d | 10.0 | 100 | 121d | 10.0 | 93 |
| 2,5-di (OCH$_3$) | 114e | 80.0 | 59 | 121e | 80.0 | 74 |
| 3-Cl | 114f | 10.0 | 100 | 121f | 80.0 | 54 |
| 3,5-di (Cl) | 114g | 2.5 | na | 121g | 80.0 | 55 |
| 3-CN | 114h | 20.0 | na | 121h | 80.0 | na |
| 4-CN | 114i | 5.0 | na | 121i | 20.0 | na |
| 4-NO$_2$ | 114j | 20.0 | na | 121j | 40.0 | na |
| 2-OCH$_3$ | 114l | 40.0 | 94 | 121l | 40.0 | 86 |
| 3,4-di (OCH$_3$) | 114m | 80.0 | na | 121m | 80.0 | 66 |
| Rifampicin | | 1.0 | | | 1.0 | |

*na = not available

Among 4-carboxaldehydes derivatives, the most effective were 114c (R=4-CH$_3$) derivatives and 114g (R=3,5-di(Cl), which showed a MIC equal to 2.5 μg/mL followed by compounds 114a (R=4-Cl), 114b (R=4-Br) and 114i (R=4-CN) with MIC equal to 5.0 μg/mL. These values of MIC are inferior to the value of 6.25 μg/mL postulated by Global Discovery Program for Novel Anti-tuberculosis Drugs as limiting in the evaluation of new prospects to inhibit *M. tuberculosis*.

A.2—Leishmanicide Evaluation

The evaluation of the Leishmanicide activity of the type I and II 1,2,3-triazole derivatives was made through in vitro essays against promastigote forms of *Leishmania amazonensis*, and after the incubation with compounds, live parasites are counted by fluorescence, thus obtaining as a result, the percentage of inhibition of the compounds evaluated.

Essays were performed in triplicate using pentamidine as a positive pattern with a 160 μg/mL concentration. Table shows us the results obtained for 114f, 114j, 121f and 121l derivatives.

TABLE 3

Percentage of parasitic inhibition

| Concentration (μg/mL) | Pentamidine | 114f | 114j | 121f | 121l |
|---|---|---|---|---|---|
| 320 | | | 72% | | No inhibition |
| 160 | 53% | | No inhibition | 11% | No inhibition |
| 80 | No inhibition | | No inhibition | No inhibition | No inhibition |
| 20 | No inhibition | | No inhibition | No inhibition | No inhibition |
| 10 | No inhibition | | No inhibition | No inhibition | 93% | No inhibition |
| 5 | No inhibition | | No inhibition | No inhibition | No inhibition | No inhibition |

Compared to pentamidine, which in a 160 μg/mL concentration presents an inhibition percentage of 53%, with the most active compound, the gem-difluormethyl 121f derivative with an inhibition percentage of 93% in a 10.0 μg/mL concentration. 114f derivative, precursor of 121f, also presented activity against the promastigote forms, with an inhibition percentage of 72%, however in a concentration superior to the pattern (pentamidine). However, derivative 114j presented an inhibition percentage 11% lower than pentamidine with the same 160.0 μg/mL concentration and o 121l did not present activity against the protozoa.

The evaluation of preliminary results suggests the presence of the chloride in 121f and 114f can be associated to the activity shown by both compounds and to the fact that the change of the aldehyde group into gem-difluormethylenic originated an increase of the leishmanicide activity.

B—Antimicrobial Evaluation of the Type III Triazole Derivatives

The antimicrobial activity of type III 1,2,3-triazole derivatives (Formula XI) was evaluated.

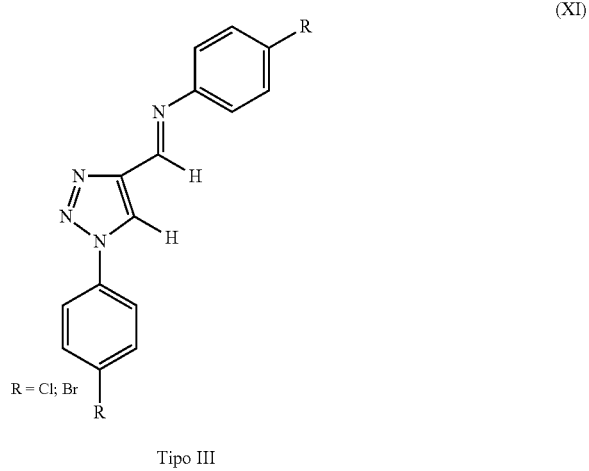

Tipo III for example,

R=Cl (AND)-4-chloride-N-((1-(4-chlorophenyl)-1H-1,2,3-triazole-4-il)methylene)benzenamine; and, R=Br (AND)-4-bromo-N-((1-(4-bromophenyl)-1H-1,2,3-triazole-4-il) methylene)benzenamine which have shown an inhibitory activity of the tuberculosis presenting a MIC of 40 μg/mL and 20 μg/mL, respectively.

Thus, three classes of compounds derived from the 1,2,3-triazole nucleus which presented high inhibitory activity in vitro, of *M. tuberculosis* H37Rv (ATCC 27294). These results, even being preliminary, the evaluation indicates that the derivatives of the 1,2,3-triazole nucleus are promising tuberculostatic agents.

EXAMPLE 2

Below there is the detailed description of the obtainment of both type I and II 1,2,3-triazole compounds, which were confirmed by analytical methods represented by Figure II.

A—Method of general obtainment of type I 1,2,3-triazole derivatives:

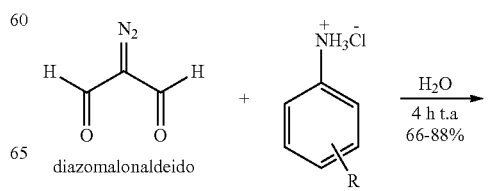

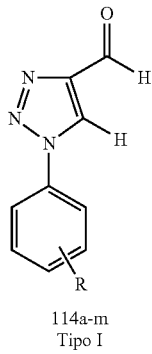

114a-m
Tipo I a. R = 4-Cl
b. R = 4-Br
c. R = 4-CH₃
d. R = 4-OCH₃
e. R = 2,5-OCH₃
f. R = 3-Cl
g. R = 3,5-Cl
h. R = 3-CN
i. R = 4-CN
j. R = 4-NO₂
l. R = 2-OCH₃
m. R = 3,4-OCH₃

(Translation: Diazomalonaldehyde)

In a balloon containing 5 mmol of diazomalonaldehyde 30.0 mL of distilled water was added. Then, a recently prepared solution with 4.5 mmol of the chloride derivative of the desired amine was added slowly into 5 mL of distilled water. The reaction mixture was under disturbance at room temperature, for 4 hours, and the precipitation of triazole product was observed. The solid was insulated by filtration and washed with ice water.

This methodology was used to obtain the below mentioned compounds:

a—4-carboxaldehyde-1-(4-chlorophenyl)-1H-1,2,3-triazole (114a)

The derivate (114a) was prepared with 75.0% of output, as of the reaction of the diazomalonaldehyde with the 4-chloroaniline chloride, thus obtaining an amorphous white solid with fusion point at 159.0-161.0° C.

⇒ $^1$H RMN (500.00 MHz; CDCl$_3$/Me$_4$Si; δ (ppm)): 7.56 (d, 2H, H3' and H5', J=1.5 and 3.0 Hz); 7.74 (d, 2H, H2' and H6', J=7.0 Hz); 8.53 (s, 1H, H5); 10.22 (s, 1H, CHO);

⇒ $^{13}$C RMN (125.0 MHz, CDCl$_3$/Me$_4$Si; δ(ppm)): 122.0 (C3' and C5'); 123.0 (C5); 130.2 (C2' and C6'); 134.6 (C1'); 135.8 (C4'); 148.2 (C4); 184.9 (CHO);

⇒ IV (KBr) cm$^{-1}$: 3094 (ν C—H$_{ar}$); 2842 (νC—H$_{aldehyde}$); 1705 (ν C=O);

⇒ EM (m/z): 207 (M$^+$; 32%); 178 (M$^+$−29; 100%); 151 (M$^+$−56; 75%); 111 (M$^+$−96; 86%); 89 (M$^+$−118; 35%); 75 (M$^+$−132; 84%);

⇒ Elementary Analysis (theoretical/experimental):
C—52.05%/52.37%;
H—2.91%/2.76%;
N—20.24%/20.64%.

b—4-carboxaldehyde-1-(4-bromophenyl)-1H-1,2,3-triazole (114b)

The derivative (114b) was prepared with 76.0% of output, as of the reaction of the diazomalonaldehyde with the 4-bromoaniline chloride, thus obtaining an amorphous white solid with fusion point at 190.0-191.0° C.

⇒ RMN de $^1$H (500.00 MHz; CDCl$_3$/Me$_4$Si; δ (ppm)): 7.68 (d, 2H, H3' and H5', J=9.0 Hz); 7.72 (d, 2H, H2' and H6', J=9.0 Hz); 8.54 (s, 1H, H5); 10.22 (s, 1H, CHO);

⇒ $^{13}$C RMN (125.0 MHz, CDCl$_3$/Me$_4$Si; δ(ppm)): 122.2 (C2' and C6'); 122.9 (C5); 123.7 (C4'); 133.2 (C3' and C5'); 135.1 (C1'); 148.2 (C4); 184.9 (CHO);

⇒ IV (KBr) cm$^{-1}$: 3098 (ν C—H$_{ar}$); 2851 (ν C—H$_{aldehyde}$); 1698 (ν C=O);

⇒ EM (m/z): 253 (M$^+$; 11%); 224 (M$^+$−29; 32%); 197 (M$^+$−56; 18%); 157 (M$^+$−96; 42%); 116 (M$^+$−137; 100%);

⇒ Elementary Analysis (theoretical/experimental):
C—42.88%/42.77%;
H—2.40%/2.36%;
N—16.67%/16.90%.

c—4-carboxaldehyde-1-(4-methylphenyl)-1H-1,2,3-triazole (114c)

The derivative (114c) was prepared with 86.0% of output, as of the reaction of the diazomalonaldehyde with 4-methylaniline chloride, thus obtaining an amorphous white solid with fusion point at 105.0-106.0° C.

⇒ $^1$H RMN (500.00 MHz; CDCl$_3$/Me$_4$Si; δ (ppm)): 2.45 (s, 1H, CH$_3$); 7.36 (d, 2H, H3' and H5', J=8.0 Hz); 7.64 (d, 2H, H2' and H6', J=8.0 Hz); 8.49 (s, 1H, H5); 10.22 (s, 1H, CHO);

⇒ $^{13}$C RMN (125.0 MHz, CDCl$_3$/Me$_4$Si; δ(ppm)): 21.1 (CH$_3$); 140.1 (C1'); 133.8 (C4'); 130.5 (C2' and C6'); 123.0 (C5); 120.7 (C3' and C5'); 148.0 (C4); 185.1 (CHO);

⇒ IV (KBr) cm$^{-1}$: 3136 (ν C—H$_{ar}$); 2842 (ν C—H$_{aldehyde}$); 1696, (ν C=O);

⇒ EM (m/z): 187 (M$^+$; 20%); 158 (M$^+$−29; 52%); 130 (M$^+$−57; 100%); 91 (M$^+$−96; 62%).

⇒ Elementary Analysis (theoretical/experimental):
C—64.16%/65.10%;
H—4.85%/4.65%;
N—22.45%/22.24%.

d—4-carboxaldehyde-1-(4-methoxyphenyl)-1H-1,2,3-triazole (114d)

The derivative (114d) was prepared with 76.0% of output, as of the reaction of the diazomalonaldehyde with the 4-metoxyaniline chloride, thus obtaining an amorphous white solid with fusion point at 158.6-161° C.

⇒ $^1$H RMN (500.00 MHz; CDCl$_3$/Me$_4$Si; δ (ppm)): 3.89 (s, 3H, OCH$_3$); 7.06 (ddd, 2H, H3' and H5', J=4.5 and 9.0 Hz); 7.66 (ddd, 2H, H2' and H6', J=4.5 and 9.0 Hz); 8.46 (s, 1H, H5); 10.21 (s, 1H, CHO);

⇒ $^{13}$C RMN (125.0 MHz, CDCl$_3$/Me$_4$Si; δ(ppm)): 55.7 (OCH3); 123.0 (C5); 129.4 (C1'); 122.4 (C2' and C6'), 115.0 (C3' and C5'); 148.5 (C4); 160.5 (C4'); 185.1 (CHO);

⇒ IV (KBr) cm$^{-1}$: 3133 (ν C—H); 2839 (ν C—H$_{aldehyde}$); 1692 (ν C=O);

⇒ EM (m/z): 203 (M$^+$; 39.5%); 174 (M$^+$−29; 40%); 160 (M$^+$−43; 79.3%); 146 (M$^+$−57; 42.3%); 132 (M$^+$−71; 100%); 77 (M$^+$−126; 40%);

⇒ Elementary Analysis (theoretical/experimental):
C—59.11%/59.55%;
H—4.43%/4.86%;
N—20.69%/20.42%.

e—4-carboxaldehyde-1-(2,5-dimethoxyphenyl)-1H-1,2,3-triazole (114e)

The derivative (114e) was prepared with 73.0% of output, as of the reaction of diazomalonaldehyde with the 2,5- dimethoxyaniline chloride (114e), thus obtaining an amorphous yellow solid with fusion point at 89.3-89.8° C.

⇒ $^1$H RMN (500.00 MHz; CDCl$_3$/Me$_4$Si; δ (ppm)): 3.85 (s, 3H, OCH$_3$); 3.88 (s, 3H, OCH$_3$); 7.01 (dd, 1H, H4', J=3 and 9 Hz); 7.06 (d, 1H, H3', J=9 Hz); 7.49 (d, 1H, H6', J=3 and 9 Hz); 8.79 (s, 1H, H5); 10.23 (s, 1H, CHO);

⇒ $^{13}$C RMN (125.0 MHz, CDCl$_3$/Me$_4$Si; δ(ppm)): 55.7 (OCH3); 123.0 (C5); 129.4 (C1'); 122.4 (C2' and C6'); 115.0 (C3' and C5'); 148.5 (C4); 160.5 (C4'); 185.1 (CHO);

⇒ IV (KBr) cm$^{-1}$: 3369 (ν C—H); 2929 (ν C—H$_{aldehyde}$); 1697 (ν C=O); 1228 (νC—O);

⇒ EM (m/z): 233 (M$^+$; 45.0%); 204 (M$^+$-29; 40%); 190 (M$^+$-43; 38.4%); 176 (M$^+$-57; 27.8%); 162 (M$^+$-71; 100%);

⇒ Elementary Analysis (theoretical/experimental):
C—56.65%/56.63%;
H—4.75%/5.56%;
N—18.02%/17.40%.

f—4-carboxaldehyde-1-(3-chlorophenyl)-1H-1,2,3-triazole (114f)

The derivative (114f) was prepared with 73.0% of output, as of the reaction of diazomalonaldehyde with the 3-chlorideaniline chloride, thus obtaining an amorphous yellow solid with fusion point at 129.4-130.5° C.

⇒ $^1$H RMN (500.00 MHz; CDCl$_3$/Me$_4$Si; δ (ppm)): 7.51 (m, 2H, H4' and H6', J=1.5; 3.0 and 8.0 Hz); 7.85 (t, 1H, H2', J=1.5 and 3.0 Hz); 7.68 (ddd, 1H, H5', J=1.5; 3.0 and 8.0 Hz); 8.55 (s, 1H, H5); 10.23 (s, 1H, CHO);

⇒ $^{13}$C RMN (125.0 MHz, CDCl$_3$/Me$_4$Si; δ(ppm)): 118.8 (C6'); 121.2 (C2'); 123.0 (C4'); 129.5 (C5); 131.1 (C5'); 135.9 (C1'); 136.9 (C3'); 148.2 (C4); 184.8 (CHO);

⇒ IV (KBr) cm$^{-1}$: 3127 (ν C—H); 2874 (ν C—H$_{aldehyde}$); 1701 (ν C=O);

⇒ EM (m/z): 207 (M$^+$; 18%); 178 (M$^+$-29; 92%); 151 (M$^+$-56; 40%); 111 (M$^+$-96; 100%); 89 (M$^+$-118; 38%); 75 (M$^+$-132; 92%);

⇒ Elementary Analysis (theoretical/experimental):
C—52.05%/52.37%;
H—2.91%/2.76%;
N—20.24%/20.64%.

g—4-carboxaldehyde-1-(3,5-dichlorophenyl)-1H-1,2,3-triazole (114g)

The derivative (114g) was prepared with 73.0% of output, as of the reaction of diazomalonaldehyde with the 3,5-dichlorideaniline chloride, thus obtaining an amorphous white solid with fusion point at 156.0-157.0° C.

⇒ $^1$H RMN (500.00 MHz; CDCl$_3$/Me$_4$Si; δ (ppm)): 7.52 (d, 1H, H4', J=1.5 Hz); 7.75 (d, 2H, H2' and H6' J=1.5 Hz); 8.75 (s, 1H, H5); 10.22 (s, 1H, CHO);

⇒ $^{13}$C RMN (125.0 MHz, CDCl$_3$/Me$_4$Si; δ(ppm)): 119.3 (C2' and C6'); 123.0 (C4'); 129.83 (C5); 136.6 (C1'); 137.3 (C4); 148.3 (C3' and C5'); 184.6 (CHO);

⇒ IV (KBr) cm$^{-1}$: 3126 (ν C—H); 3085 (ν C—H$_{aldehyde}$); 1690 (ν C=O);

⇒ EM (m/z): 241 (M$^+$; 18%); 212 (M$^+$-29; 100%); 145 (M$^+$-96; 50%); 109 (M$^+$-132; 42%);

⇒ Elementary Analysis (theoretical/experimental):
C—44.66%/44.91%;
H—2.08%/2.19%;
N—17.36%/16.70%.

h—4-carboxaldehyde-1-(3-cyanophenyl)-1H-1,2,3-triazole (114h)

The derivative (114h) was prepared with 80.0% of output, as of the reaction of diazomalonaldehyde with the chloride of 3-cyanoaniline, thus obtaining an amorphous white solid with fusion point at 177.7-179.8° C.

⇒ $^1$H RMN (500.00 MHz; CDCl$_3$/Me$_4$Si; δ (ppm)): 7.75 (t, 1H, H5', J=8 Hz, 0.5 Hz); 8.06 (ddd, 1H, H6', J=1, 2 and 8 Hz); 7.84 (dt, 1H, H4', J=1 and 8 Hz); 8.15 (t, 1H, H2', J=2 Hz); 8.61 (s, 1H, H5); 10.24 (s, 1H, CHO);

⇒ $^{13}$C RMN (125.0 MHz, CDCl$_3$/Me$_4$Si; δ(ppm)): 114.6 (C3'); 117.0 (CN); 124.7 (C5); 133.1 (C5'); 124.1 (C2'); 131.2 (C6'); 122.9 (C4'); 136.7 (C1'); 148.0 (C4); 184.6 (CHO);

⇒ IV (KBr) cm$^{-1}$: 3130 (ν C—H); 2839 (ν C—H$_{aldehyde}$); 2234 (ν CN); 1697 (ν C=O);

⇒ EM (m/z): 198 (M$^+$; 9%); 212 (M$^+$-29; 100%); 142 (M$^+$-56; 40%); 115 (M$^+$-83; 94%); 102 (M$^+$-96; 42%);

⇒ Elementary Analysis (theoretical/experimental):
C—60.60%/60.72%;
H—3.05%/3.32%;
N—28.27%/28.15%.

i—4-carboxaldehyde-1-(4-cyanophenyl)-1H-1,2,3-triazole (114i)

The derivative (114i) was prepared with 75.0% of output, as of the reaction of diazomalonaldehyde with the 4-cyanoaniline chloride, thus obtaining an amorphous white solid with fusion point at 178.9-179.6° C.

⇒ $^1$H RMN (500.00 MHz; DMSO$_{d6}$/Me$_4$Si; δ (ppm)): 8.14 (d, 2H, H3' and H5', J=9 Hz); 8.24 (d, 2H, H2' and H6', J=9 Hz); 9.71 (s, 1H, H5); 10.14 (s, 1H, CHO);

⇒ $^{13}$C RMN (125.0 MHz, DMSO$_{d6}$/Me$_4$Si; δ(ppm)): 111.8 (C4'); 117.8 (CN); 126.4 (C5); 121.1 (C2' and C6'); 134.2 (C3' and C5'); 138.8 (C1'); 1473.6 (C4); 184.6 (CHO);

⇒ IV (KBr) cm$^{-1}$: 3116 (ν C—H); 2865 (ν C—H$_{aldehyde}$); 2232 (ν CN); 1697 (ν C=O);

⇒ EM (m/z): 198 (M$^+$; 10%); 169 (M$^+$-29; 96%); 142 (M$^+$-56; 48%); 115 (M$^+$-83; 40%); 102 (M$^+$-96; 100%);

⇒ Elementary Analysis (theoretical/experimental):
C—60.60%/60.32%;
H—3.05%/3.16%;
N—28.27%/28.66%.

j—4-carboxaldehyde-1-(4-nitrophenyl)-1H-1,2,3-triazole (114j)

The derivative (114j) was prepared with 80.0% of output, as of the reaction of diazomalonaldehyde with the 4-nitroaniline chloride (114j), thus obtaining an amorphous yellow solid with fusion point at 185.0-186.0° C.

⇒ $^1$H RMN (500.00 MHz; DMSO$_{d6}$/Me$_4$Si; δ (ppm)): 8.31 (d, 2H, H2' and H6', J=8.8 Hz); 8.48 (d, 2H, H3' and H5', J=8.8 Hz); 9.78 (s, 1H, H5); 10.15 (s, 1H, CHO);

⇒ $^{13}$C RMN (125.0 MHz, DMSO$_{d6}$/Me$_4$Si; δ (ppm)): 121.4 (C2' and C6'); 125.4 (C3' and C5'); 126.7 (C5); 140.2 (C4); 147.2 (C1'); 147.7 (C4'); 184.8 (CHO);

⇒ IV (KBr) cm$^{-1}$: 3136.18 (ν C—H$_{ar}$); 1696.21 (νC=O); 1524.18 (νNO$_2$); 1348.96 (νNO$_2$); 856.83 (νN=O); 785 (νN=O);

⇒ EM (m/z): 218 (M$^+$; 9%); 189 (M$^+$-29; 100%); 143 (M$^+$-75; 60%); 116 (M$^+$-102; 52%);

⇒ Elementary Analysis (theoretical/experimental):
C—49.55%/49.91%;
H—2.77%/2.94%;
N—25.68%/25.60%.

l—4-carboxaldehyde-1-(2-methoxyphenyl)-1H-1,2,3-triazole (114l)

The derivative (114l) was prepared with 66.0% of output, as of the reaction of diazomalonaldehyde with the 2-methoxyaniline chloride, thus obtaining an amorphous yellowish solid with fusion point at 108.0-109.5° C.

⇒ $^1$H RMN (500.00 MHz; CDCl$_3$/Me$_4$Si; δ (ppm)): 3.93 (s, 3H, OCH$_3$); 7.15 (m, 2H, H4' and H5', J=1.0; 6.5 and 8.0

Hz); 7.47 (ddd, 1H, H3', J=1.5 and 8.0 Hz); 7.87 (dd, 1H, H6', J=1.5; 6.5 and 8.0 Hz); 8.72 (s, 1H, H5); 10.24 (s, 1H, CHO);
⇒ $^{13}$C RMN (125.0 MHz, CDCl$_3$/Me$_4$Si; δ(ppm)): 56.0 (OCH$_3$); 112.3 (C3'); 125.2 (C1' and C6'); 121.3 (C5'); 130.9 (C4'); 127.3 (C5); 147.3 (C4); 150.8 (C2'); 185.3 (CHO);
⇒ IV (KBr) cm$^{-1}$: 3157 (ν C—H); 2979 (ν C—H$_{aldehyde}$); 1685 (ν C=O);
⇒ EM (m/z): 203 (M$^+$; 38%); 174 (M$^+$-29; 30%); 160 (M$^+$-43; 60%); 146 (M$^+$-57; 72%); 104 (M$^+$-99; 70%); 77 (M$^+$-126; 100%);
⇒ Elementary Analysis (theoretical/experimental):
C—59.11%/58.62%;
H—4.43%/4.56%;
N—20.69%/20.38%.

m—4-carboxaldehyde
1-(3,4-dimethoxyphenyl)-1H-1,2,3-triazole (114m)

The derivative (114m) was prepared with 80.0% of output, as of the reaction of diazomalonaldehyde with the 3,4-dimethoxyaniline chloride, thus obtaining an amorphous yellow solid with fusion point at 170.0-171.0° C.
⇒ $^1$H RMN (500.00 MHz; CDCl$_3$/Me$_4$Si; δ (ppm)): 3.96 (s, 3H, OCH$_3$); 3.98 (s, 3H, OCH$_3$); 6.99 (d, 1H, H5', J=8.5 Hz); 7.23 (dd, 1H, H2', J=2.5 and 8.5 Hz); 7.36 (d, 1H, H2', J=2.5 Hz); 8.49 (s, 1H, H5); 10.21 (s, 1H, CHO);
⇒ $^{13}$C RMN (125.0 MHz, CDCl$_3$/Me$_4$Si; δ(ppm)): 56.2 (3' or 4'-OCH$_3$); 56.3 (3' or 4'-OCH$_3$); 105.0 (C2'); 111.2 (C5'); 112.8 (C6'); 129.5 (C1'); 123.1 (C5); 148.0 (C4); 149.9 (C4'); 150.1 (C3'); 185.1 (CHO);
⇒ IV (KBr) cm$^{-1}$: 3131 (ν C—H); 2970 (ν C—H$_{aldehyde}$); 1693 (ν C=O);
⇒ EM (m/z): 233 (M$^+$; 50%); 204 (M$^+$-29; 9%); 190 (M$^+$-43; 80%); 176 (M$^+$-57; 30%); 162 (M$^+$-71; 100%);
⇒ Elementary Analysis (theoretical/experimental):
C—56.55%/55.95%;
H—4.72%/4.96%;
N—18.02%/17.88%.

B. General Method of Obtainment of Type II 1,2,3-Triazole Derivatives

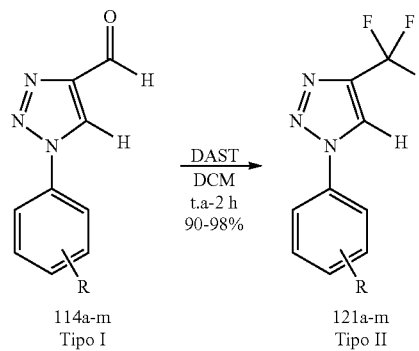

114a-m
Tipo I 121a-m
Tipo II a. R = 4-Cl
b. R = 4-Br
c. R = 4-CH$_3$
d. R = 4-OCH$_3$
e. R = 2,5-OCH$_3$
f. R = 3-Cl
g. R = 3,5-Cl
h. R = 3-CN
i. R = 4-CN
j. R = 4-NO$_2$
l. R = 2-OCH$_3$
m. R = 3,4-OCH$_3$ Translation: Type I Type II In a 50 mL volumetric flask, 7.5 mmol of the derivative 4-carboxaldehyde triazole and 15.0 mL of dry dichloromethane was added. After complete dissolution of the starting compound, 15.0 mmol of DAST was slowly added, at room temperature. The resulting reaction mixture was shaken at room temperature and followed-up by c.c.f., using ethyl hexane/acetate (7:3) as eluant, and after approximately two hours of reaction, there was the complete consume of the starting material. The reaction mixture was poured out in 20.0 mL of an iced solution of sodium bicarbonate and extracted with dichloromethane (3×15 mL). Organic stages were combined and washed with a saturated solution of sodium chloride (2×10.0 mL) and distilled water (2×10.0 mL). The organic stage was dried out with anhydrous sodium sulfate and the solvent evaporated in vacuum. The residue obtained was purified by a chromatographic column using chloroform as eluant.

This methodology was employed to obtain of the below mentioned compounds:

a—1-(4-chlorophenyl)-4-difluoromethyl-1H-1,2,3-triazole (121a)

The derivative 121a was prepared with 95.0% of output, as of the reaction of fluoridation of the derivative 4-carboxaldehyde-1-(4-chlorophenyl)-1H-1,2,3-triazole (114a) with the diethylamino sulphur trifluoride, DAST, obtaining a white solid with fusion point of 122.0-124.0° C.
⇒ $^1$H RMN (500.00 MHz; CDCl$_3$/Me$_4$Si; δ (ppm)): 6.95 (t, 1H, CF$_2$H, J=54.5 Hz); 7.71 (d, 2H, H3' and H5', J=7.0 Hz); 7.54 (d, 2H, H2' and H6', J=7.0 Hz); 8.21 (s, 1H, H5);
⇒ $^{13}$C RMN (125.0 MHz, CDCl$_3$/Me$_4$Si; δ (ppm)): 109.9 (t, CF$_2$H, J=236.5 Hz); 120.5 (C5); 134.9 (C1'); 135.4 (C4'); 122.0 (C2' and C6'); 130.1 (C3' and C5'); 143.7 (t, C4, J=28.1 Hz);
⇒ $^{19}$F RMN (376.0 MHz, CDCl$_3$/CFCl$_3$; δ (ppm)): −112.5 (2F, CHF$_2$);
⇒ IV (KBr) cm$^{-1}$: 3150 (ν C—H); 1046 (ν C—F);
⇒ EM (m/z): 229 (M$^+$; 60%); 220 (M$^+$-29; 68%); 182 (M$^+$-47; 80%); 137 (M$^+$-92; 67%); 111 (M$^+$-118; 100%); 75 (M$^+$-154; 90%),
⇒ Elementary Analysis (theoretical/experimental):
C—47.08%/47.62%;
H—2.63%/3.30%;
N—18.30%/16.02%.

b—1-(4-bromophenyl)-4-difluoromethyl-1H-1,2,3-triazole (121b)

The derivative 121b was prepared with 95.0% of output, as of the reaction of the fluoridation of the derivative 4-carboxaldehyde-1-(4-bromophenyl)-1H-1,2,3-triazole (114b) with the diethylamino sulphur trifluoride, DAST, thus obtaining a white solid with fusion point at 141.0-144.0° C.
⇒ $^1$H RMN (500.00 MHz; CDCl$_3$/Me$_4$Si; δ (ppm)): 6.94 (t, 1H, CF$_2$H, J=68.0 Hz); 7.64 (d, 2H, H3' and H5', J=11.0 Hz); 7.69 (d, 2H, H2' and H6', J=11.0 Hz); 8.20 (s, 1H, H5).
⇒ $^{13}$C RMN (125.0 MHz, CDCl$_3$/Me$_4$Si; δ (ppm)): 109.5 (t, CF$_2$H, J=233.2 Hz); 120.4 (C5); 135.5 (C1'); 122.2 (C3' and C5'); 133.6 (C4'); 133.1 (C2' and C6'); 143.7 (t, C4, J=28.5 Hz).
⇒ $^{19}$F RMN (376.0 MHz, CDCl$_3$/CFCl$_3$; δ (ppm)): −112.5 (2F, CHF$_2$);
⇒ IV (KBr) cm$^{-1}$: 1497 (δ C-Har); 1043 (ν C—F);

⇒ EM (m/z): 273 (M⁺; 85%); 245 (M⁺−28; 33%); 226 (M⁺−49; 60%); 181 (M⁺−94; 50%); 154 (M⁺−119; 83%); 166 (M⁺−109; 100%);
⇒ Elementary Analysis (theoretical/experimental):
C—39.44%/39.66%;
H—2.04%/2.14%;
N—15.33%/15.16%.

c—1-(4-methylphenyl)-4-difluoromethyl-1H-1,2,3-triazole (121c)

The derivative (121c) was prepared with 93.0% of output, as of the reaction of fluoridation of the derivative 4-carboxaldehyde-1-(4-methylphenyl)-1H-1,2,3-triazole (114c) with the diethylamino sulphur trifluoride DAST, thus obtaining a white solid with fusion point at 96.5-97.5° C.

⇒ $^1$H RMN (500.00 MHz; CDCl$_3$/Me$_4$Si; δ (ppm)): 2.43 (s, 1H, CH$_3$); 6.94 (t, 1H, CF$_2$H, J=54.5 Hz) 7.31 (d, 2H, H3' and H5', J=8.8 Hz); 7.60 (d, 2H, H2' and H6', J=8.8 Hz); 8.18 (s, 1H, H5);
⇒ $^{13}$C RMN (125.0 MHz, CDCl$_3$/Me$_4$Si; δ (ppm)): 20.5 (CH$_3$); 109.5 (t, CF$_2$H, J=233.4 Hz); 119.9 (C5); 139.1 (C1'); 133.6 (C4'); 129.8 (C2' and C6'); 120.1 (C3' and C5'); 142.7 (t, C4, J=28.5 Hz);
⇒ $^{19}$F RMN (376.0 MHz, CDCl$_3$/CFCl$_3$; δ (ppm)): −112.3 (2F, CHF$_2$);
⇒ IV (KBr) cm$^{-1}$: 3162 (ν C—H); 1031 (ν C—F);
⇒ EM (m/z): 209 (M⁺; 42%); 180 (M⁺−29; 68%); 162 (M⁺−47; 40%); 130 (M⁺−79; 42%); 91 (M⁺−118; 100%);
⇒ Elementary Analysis (theoretical/experimental):
C—57.41%/57.83%;
H—4.34%/4.54%;
N—20.09%/19.97%.

d—1-(4-methoxyphenyl)-4-difluoromethyl-1H-1,2,3-triazole (121d)

The derivative 121d was prepared with 97.0% of output, as of the fluoridation reaction to the derivative 4-carboxaldehyde-1-(4-methoxyphenyl)-1H-1,2,3-triazole (114d) with the diethylamino sulphur trifluoride, DAST, thus obtaining a white solid with fusion point at 98.2-100.0° C.

⇒ $^1$H RMN (500.00 MHz; CDCl$_3$/Me$_4$Si; δ (ppm)): 3.89 (s, 3H, 2' OCH$_3$); 6.95 (t, 1H, CHF$_2$, J=55.0 Hz); 7.04 (dd; 2H, H3' and H5'; J=2.0 and 7.0 Hz); 7.63 (dd, 2H, H2' and H6', J=2.0 and 7.0 Hz); 8.14 (s1, 1H, H5);
⇒ $^{13}$C RMN (125.0 MHz, CDCl$_3$/Me$_4$Si; δ (ppm)): 55.6 (3H, OCH$_3$); 110.1 (t, CHF$_2$, J=234.7 Hz); 115.0 (C3' and C5'); 120.6 (C5); 122.5 (C2' and C6'); 160.3 (C4'); 129.8 (C1'); 143.2 (t, C4, J=29.1 Hz);
⇒ $^{19}$F RMN (376.0 MHz, CDCl$_3$/CFCl$_3$; δ (ppm)): −112.2 (2F, CHF$_2$);
⇒ IV (KBr) cm$^{-1}$: 3097 (ν C—H); 1051 (ν C—F); 1023 (ν C—O);
⇒ EM (m/z): 225 (M⁺; 36%); 197 (M⁺−28; 15%); 182 (M⁺−43; 100%); 154 (M⁺−71; 39%);
⇒ Elementary Analysis (calculated/experimental):
C—53.33%/53.80%;
H—4.03%/4.50%;
N—18.66%/18.40%.

e—1-(2,5-dimethoxyphenyl)-4-difluoromethyl-1H-1,2,3-triazole (121e)

The derivative 121e was prepared with 98.0% of output, as of the fluoridation reaction to the derivative 4-carboxaldehyde-1-(2,5-dimethoxyphenyl)-1H-1,2,3-triazole (114e) with the diethylamino sulphur trifluoride, DAST, thus obtaining a white solid with fusion point at 78.0-79.0° C.

⇒ $^1$H RMN (500.00 MHz; CDCl$_3$/Me$_4$Si; δ (ppm)): 3.84 (s, 3H, 5' OCH$_3$); 3.88 (s, 3H, 2' OCH$_3$) 6.97 (t, 1H, CHF$_2$, J=55.0 Hz); 6.99 (dd, 1H, H4', J=3.0 Hz); 7.04 (d; 1H, H3', J=3.0 Hz); 7.43 (d, 1H, H6', J=3.0 Hz); 8.43 (s, 1H, H5);
⇒ $^{13}$C RMN (125.0 MHz, CDCl$_3$/Me$_4$Si; δ (ppm)): *55.9 (3H, 3'OCH$_3$); *56.5 (3H, 5'OCH$_3$); 110.3 (t, CF$_2$H, J=230.0 Hz); 113.6 (C4'); 116.2 (C3' and C6'); 124.4 (C5); 121.1 (C6'); 127.3 (C1'); 142.3 (t, C4, J=29.1 Hz) 144.7 (C2'); 153.9 (C5');
⇒ $^{19}$F RMN (376.0 MHz, CDCl$_3$/CFCl$_3$; δ (ppm)): −112.2 (2F,CHF$_2$);
⇒ IV (KBr) cm$^{-1}$: 3169 (ν C—H); 1027 (ν C—F and C—O);
⇒ EM (m/z): 255 (M⁺; 60%); 227 (M⁺−28; 8%); 226 (M⁺−29; 5%); 212 (M⁺−43; 100%);
⇒ Elementary Analysis (theoretical/experimental):
C—51.77%/51.85%;
H—4.34%/4.58%;
N—16.46%/16.76%.

f—1-(3-chlorophenyl)-4-difluoromethyl-1H-1,2,3-triazole (121f)

The derivative 121f was prepared with 93.0% of output, as of the reaction of fluoridation to the derivative 4-carboxaldehyde-1-(3-chlorophenyl)-1H-1,2,3-triazole (114f) with the diethylamino sulphur trifluoride, DAST, thus obtaining a white solid with fusion point at 57.6-58.2° C.

⇒ $^1$H RMN (500.00 MHz; CDCl$_3$/Me$_4$Si; δ (ppm)): 6.96 (t, 1H, CHF$_2$, J=54.5 Hz); 7.81 (d, 1H, H2', J=1.5 Hz); 7.66 (dd, 1H, H4', J=1.2 and 7.5 Hz); *7.65 (m; 1H, H5', J=2.4 and 8.0 Hz); *7.65 (m, 2H, H6', J=2.4 and 8.0 Hz); 8.24 (s, 1H, H5).
⇒ $^{13}$C RMN (125.0 MHz, CDCl$_3$/Me$_4$Si; δ (ppm)): 109.8 (t, CF$_2$H, J=236.5 Hz); 120.5 (C5); 118.8 (C2'); 121.1 (C6'); 131.0 (C5'); 135.4 (C4'); 137.2 (C1'); 143.6 (t, C4, J=28.1 Hz); 135.8 (C3');
⇒ $^{19}$F RMN (376.0 MHz, CDCl$_3$/CFCl$_3$; δ (ppm)): −112.6 (2F,CHF$_2$);
⇒ IV (KBr) cm$^{-1}$: 3146 (ν C—H); 1042 (ν C—F);
⇒ EM (m/z): 229 (M;⁺ 60%); 200 (M*⁺−29; 72%); 182 (M*⁺−47; 60%); 137 (M*⁺−92; 50%); 111 (M*⁺−118; 100%); 75 (M*⁺−154; 70%);
⇒ Elementary Analysis (theoretical/experimental):
C—47.08%/47.38%;
H—2.63%/2.89%;
N—18.30%/17.78%.

g—1-(3,5-dichlorophenyl)-4-difluoromethyl-1H-1,2,3-triazole (121g)

The derivative 121g was prepared with 98.0% of output, as of the reaction of fluoridation to the derivative 4-carboxaldehyde-1-(3,4-dichlorophenyl)-1H-1,2,3-triazole (114 g) with the diethylamino sulphur trifluoride, DAST, thus obtaining a white solid with fusion point at 83.0-85.0° C.

⇒ $^1$H RMN (500.00 MHz; CDCl$_3$/Me$_4$Si; δ (ppm)): 6.95 (t, 1H, CHF$_2$, J=54.5 Hz); 7.72 (d, 1H, H2', J=1.5 Hz); 7.49 (dd, 1H, H4', J=1.0 and 1.5 Hz); 7.72 (d, 1H, H6', J=1.5 Hz); 8.24 (s, 1H, H5).
⇒ $^{13}$C RMN (125.0 MHz, CDCl$_3$/Me$_4$Si; δ (ppm)): 109.6 (t, CHF$_2$, J=235.3 Hz); 119.2 (C2' and C6'); 123.0 (C5); 129.5 (C4'); 136.5 (C3' and C5'); 137.6 (C1'); 143.9 (t, C4, J=29.8 Hz).

⇒ ¹⁹F RMN (376.0 MHz, CDCl₃/CFCl₃; δ (ppm)): −117.6 (2F, CHF₂)
⇒ IV (KBr) cm⁻¹: 3160 (ν C—H); 1042 (ν C—F);
⇒ EM (m/z): 263 (M⁺; 73%); 235 (M⁺−28; 30%); 234 (M⁺−29; 100%); 216 (M⁺−47; 70%);
⇒ Elementary Analysis (calculated/experimental):
C—40.94%/41.19%;
H—1.91%/2.32%;
N—15.91%/14.41% h—1-(3-cyanophenyl)-4-difluoromethyl-1H-1,2,3-triazole (121h)

The derivative 121h was prepared with 97.0% of output, as of the reaction of fluoridation to the derivative 4-carboxaldehyde-1-(3-cyanophenyl)-1H-1,2,3-triazole (114h) with the diethylamino sulphur trifluoride, DAST, thus obtaining a white solid with fusion point at 119.0-120.0° C.
⇒ ¹H RMN (500.00 MHz; CDCl₃/Me₄Si; δ (ppm)): 6.97 (t, 1H, CHF₂, J=54.5 Hz); 8.12 (dd, 1H, H2', J=1.5 and 2.0 Hz); 8.06 (ddd, 1H, H4', J=1.0; 2.0; 3.0 and 8.5 Hz); 7.81 (dd, 1H, H6', J=1.0 and 7.0 Hz); 7.74 (d, 1H, H5', J=8.0 Hz); 8.33 (s, 1H, H5);
⇒ ¹³C RMN (125.0 MHz, CDCl₃/Me₄Si; δ (ppm)): 109.6 (t, CHF₂, J=237.3 Hz); 114.4 (C3'); 117.1 (CN); 120.0 (C5); 124.0 (C5'); 124.7 (C6'); 131.1 (C4'); 132.8 (C2'); 137.0 (C1'); 143.9 (t, C4, J=29.5 Hz);
⇒ ¹⁹F RMN (376.0 MHz, CDCl₃/CFCl₃; δ (ppm)): −112.9 (2F, CHF₂)
⇒ IV (KBr) cm⁻¹: 3156 (ν C—H); 2235 (ν CN); 1042 (ν C—F);
⇒ EM (m/z): 220 (M⁺; 24%); 192 (M⁺−28; 20%); 191 (M⁺−29; 63%); 173 (M⁺−47; 52%); 128 (M⁺−92; 45%); 102 (M⁺−118; 100%);
⇒ Elementary Analysis (calculated/experimental):
C—54.55%/55.10%;
H—2.75%/2.95%;
N—25.45%/24.70%.

i—1-(4-cyanophenyl)-4-difluoromethyl-1H-1,2,3-triazole (121i)

The derivative 121i was prepared with 98.0% of output, as of the reaction of fluoridation to the derivative 4-carboxaldehyde-1-(4-cyanophenyl)-1H-1,2,3-triazole (114i) with the diethylamino sulphur trifluoride, DAST, thus obtaining a white solid with fusion point at 126.0-128.0° C.
⇒ ¹H RMN (500.00 MHz; CDCl₃/Me₄Si; δ (ppm)): 6.97 (t, 1H, CHF₂, J=54.5 Hz); 7.89 (dd, 2H, H3' and H5', J=2.0 and 7.0 Hz); 7.96 (dd, 1H, H2' and H6', J=1.5 and 7.0 Hz); 8.35 (s, 1H, H5);
⇒ ¹³C RMN (125.0 MHz, CDCl₃/Me₄Si; δ (ppm)): 109.7 (t, CHF₂, J=235.0 Hz); 114.4 (C3'); 117.1 (CN); 120.0 (C5); 124.0 (C5'); 124.7 (C6'); 131.1 (C4'); 132.8 (C2'); 137.0 (C1'); 143.9 (t, C4, J=29.1 Hz);
⇒ ¹⁹F RMN (376.0 MHz, CDCl₃/CFCl₃; δ (ppm)): −112.9 (2F,CHF₂);
⇒ IV (KBr) cm⁻¹: 3139 (ν C—H); 2235 (ν CN); 1040 (ν C—F);
⇒ EM (m/z): 220 (M⁺; 42%); 192 (M⁺−28; 42%); 191 (M⁺−29; 100%); 173 (M⁺−47; 74%); 128 (M⁺−92; 58%); 102 (M⁺−118; 92%);
⇒ Elementary Analysis (calculated/experimental):
C—54.55%/55.15%;
H—2.75%/2.84%;
N—25.45%/22.68%.

j—1-(4-nitrophenyl)-4-difluoromethyl-1H-1,2,3-triazole (121j)

The derivative (121j) was prepared with 93.0% of output, as of the reaction of fluoridation to the derivative 4-carboxaldehyde-1-(4-nitrophenyl)-1H-1,2,3-triazole (114j) with the diethylamino sulphur trifluoride, DAST, thus obtaining an amorphous yellow solid with fusion point at 161.0-163.0° C.
⇒ ¹H RMN (500.00 MHz; DMSO_{d6}/Me₄Si; δ (ppm)): 6.98 (t, 1H, CF₂H, J=54.5 Hz); 8.02 (d, 2H, H2' and H6', J=7.5 Hz); 8.47 (d, 2H, H3' and H5', J=7.5 Hz); 8.35 (s, 1H, H5);
⇒ ¹³C RMN (125.0 MHz, DSMO_{d6}/Me₄Si; δ (ppm)): 109, δ (t, CF₂H, J=236.9 Hz); 120.5 (C5); 120.9 (C2' and C6'); 125.6 (C3' and C5'); 140.5 (C1'); 144.2 (C4); 147.7 (C4').
⇒ ¹⁹F RMN (376.0 MHz, DMSO_{d6}/CFCl₃; δ (ppm)): −113.0 (2F, CHF₂)
⇒ IV (KBr) cm⁻¹: 3142 (ν C—H_{ar}); 1526 (νNO₂); 1341 (νNO₂); 1039 (ν C—F);
⇒ EM (m/z): 240 (M⁺; 30%); 212 (M⁺−28; 40%); 211 (M⁺−29; 32%); 193 (M⁺−47; 18%); 166 (M⁺−74; 28%); 76 (M⁺−164; 100%);
⇒ Elementary Analysis (theoretical/experimental):
C—45.01%/44.76%;
H—2.53%/3.01%;
N—23.33%/22.53%.

l—1-(2-methoxyphenyl)-4-difluoromethyl-1H-1,2,3-triazole (121l)

The derivative 121l was prepared with 96.0% of output, as of the reaction of fluoridation to the derivative 4-carboxaldehyde-1-(2-methoxyphenyl)-1H-1,2,3-triazole (114l) with the diethylamino sulphur trifluoride, DAST, thus obtaining a white solid with fusion point at 65.0-66.0° C.
⇒ ¹H RMN (400.00 MHz; CDCl₃/Me₄Si; δ (ppm)): 3.92 (d, ¹H, OCH₃, J=4.0); 6.97 (t, CHF₂, J=72.0 Hz); 7.12 (d, 2H, H4' eH5', J=8.0 Hz); 7.46 (ddd, 1H, H3', J=4.0 and 8.0 Hz); 7.79 (d, 1H, H6', J=8.0 Hz);
⇒ ¹³C RMN (100.0 MHz; CDCl₃/Me₄Si; δ (ppm)): 56.0 (3H, OCH₃); 110.3 (t, CHF₂, J=235.0 Hz); 112.3 (C3'); 124.4 (C5); 121.3 (C5'); 125.4 (C6'); 130.6 (C4'); 151.0 (C2'); 137.0 (C1'); 142.2 (t, C4);
⇒ ¹⁹F RMN (376.0 MHz; CDCl₃/CFCl₃; δ (ppm)): −112.1 (2F,CHF₂);
⇒ IV (KBr) cm⁻¹: 3160 (ν C—H); 1035 (ν C—F);
⇒ EM (m/z): 225 (M⁺; 90%); 196 (M⁺−29; 18%); 182 (M⁺−43; 80%); 163 (M⁺−62; 20%); 154 (M⁺−71; 48%); 132 (M⁺−93; 58%); 92 (M⁺−133; 72%); 77 (M⁺−148; 98%); 51 (M⁺−174; 100%);
⇒ Elementary Analysis (calculated/experimental):
C—53.33%/53.71%;
H—4.03%/4.52%;
N—18.66%/18.70%.

m—1-(3,4-dimethoxyphenyl)-4-difluoromethyl-1H-1,2,3-triazole (121m)

The derivative 121m was prepared with 95.0% of output of the reaction of fluoridation of the derivative 4-carboxaldehyde-1-(3,4-dimethoxyphenyl)-1H-1,2,3-triazole (114m) with the diethylamino sulphur trifluoride, DAST, thus obtaining a white solid with fusion point at 62.5-63.5° C.
⇒ ¹H RMN (500.00 MHz; CDCl₃/Me₄Si; δ (ppm)): 3.96 (s, 6H, 3'OCH₃ and 4'OCH₃); 6.95 (t, 1H, CHF₂, J=54.3 Hz);

6.97 (d, 1H, H5', J=9.0 Hz); 7.33 (d, 1H, H2', J=2.5 Hz); 7.18 (dd, 1H, H6', J=2.5 and 8.5 Hz); 8.16 (s1, 1H, H5).

⇒ $^{13}$C RMN (125.0 MHz, CDCl$_3$/Me$_4$Si; δ (ppm)): 56.2 (6H, 3'OCH$_3$ and 5'OCH$_3$); 110.0 (t, CF$_2$H, J=234.5 Hz); 120.7 (C$\overline{5}$); 111.1 (C2'); 112.8 (C6'); 10$\overline{5}$.1 (C5'); 129.9 (C1'); 143.2 (t, C4, J=29.0 Hz); 149.8 (C3' and C4').

⇒ $^{19}$F RMN (376.0 MHz, CDCl$_3$/CFCl$_3$; δ (ppm)): −112.2 (2F,CHF$_2$)

⇒ IV (KBr) cm$^{-1}$: 3160 (ν C—H); 1035 (ν C—F);

⇒ EM (m/z): 255 (M$^+$; 60%); 277 (M$^+$−28; 8%); 226 (M$^+$−29; 5%); 208 (M$^+$−47; 6%);

⇒ Elementary Analysis (theoretical/experimental):

C—51.77%/51.96%;

H—4.34%/4.96%;

N—16.46%/16.10%.

C—General Method of obtainment of type III 1,2,3-triazole derivatives

Below you will find a detailed description of the obtainment of type III compounds that were confirmed by analytical methods represented by FIG. 3.

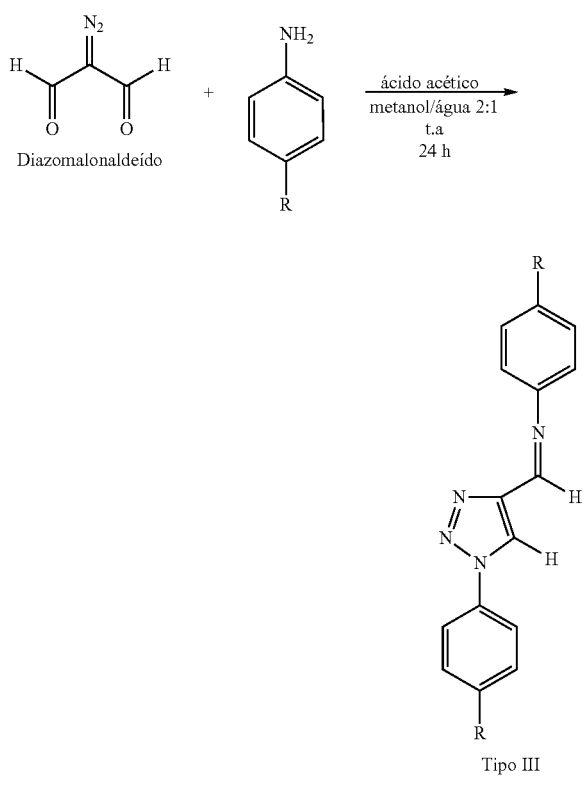

R = a. 4-Cl; b. 4-Br

In a rounded bottom 50 mL balloon containing 1.1 mol of diazomalonaldehyde dissolved in a 2:1 solution of methanol/water, 1.0 mol of the desired derivative aniline and 0.1 mL of acetic acid were added. The reaction was maintained under disturbance, at room temperature and after 24 h the solvent was evaporated and the product insulated. This methodology was used to obtain the below mentioned compounds:

1. (E)-4-chloride-N-((1-(4-chlorophenyl)-1H-1,2,3-triazole-4-il)methylene)benzenamine (119)

The derivative (119) was prepared with 73.0% of output, as of the reaction of diazomalonaldehyde with p-chloride-aniline, in an acid environment, thus obtaining an amorphous yellow solid with fusion point at 208° C.

⇒ $^1$H RMN (500.00 MHz; CDCl$_3$/Me$_4$Si; δ (ppm))*: 7.09 (d, 2H, H2" and H6", J=9 Hz); 7.19 (d, 2H, H3" and H5", J=9 Hz); 7.54 (d, 2H, H2' and H6', J=9 Hz); 7.74 (d, 2H, H3' and H5', J=9 Hz); 8.57 (s, 1H, HCN); 8.71 (s, 1H, H5);

⇒ $^{13}$C RMN (125.0 MHz, CDCl$_3$/Me$_4$Si; δ(ppm)): 121.0 (C5); 121.7 (C2" and C6"); 122.2 (C3" and C5"); 129.4 (C3" and C5"); 130.1 (C3' and C5'); 132.4 (C1'); 135.2 (C4"); 135.2 (C4'); 116.2 (C4); 147.1 (C1"); 151.8 (CHN);

⇒ IV (KBr) cm$^{-1}$: 3111 (ν C—H$_{ar}$); 1635 (ν C—H$_{imina}$);

⇒ EM (m/z):): 316 (M$^+$; 27%); 287 (M$^+$−29; 100%); 218 (M$^+$−98; 50%); 111 (M$^+$−205; 95%).

2. (E)-4-bromo-N-((1-(4-bromophenyl)-1H-1,2,3-triazole-4-il)methylene)benzenamine (120)

The derivative (120) was prepared with 80.0% of output, as of the reaction of diazomalonaldehyde with the p-bromoaniline, in an acid environment, thus obtaining an amorphous yellow solid with fusion point at 208-210.0° C.

⇒ $^1$H RMN (500.00 MHz; CDCl$_3$/Me$_4$Si; δ (ppm))*: 7.20 (d, 2H, H2" and H6", J=9.0 and 2.0 Hz); 7.38 (dd, 2H, H3" and H5", J=9.0 and 2.0 Hz); 7.55 (dd, 2H, H2' and H6', J=9.0 and 2.0 Hz); 7.75 (dd, 2H, H3' and H5', J=9.0 and 2.0 Hz); 8.58 (s, 1H, HCN); 8.71 (s, 1H, H5);

⇒ $^{13}$C RMN (125.0 MHz, CDCl$_3$/Me$_4$Si; δ(ppm)): 121.0 (C5); 121.7 (C2" and C6"); 122.2 (C2' and C6'); 129.4 (C3" and C5"); 130.1 (C3' and C5'); 132.4 (C1'); 135.0 (C4"); 135.2 (C4'); 147.4 (C4); 149.3 (C1"); 151.8 (CHN);

⇒ IV (KBr) cm$^{-1}$: 3109 (ν C—H$_{ar}$); 1635 (ν C—H$_{imina}$);

⇒ EM (m/z): 406 (M$^+$; 5%); 377 (M$^+$−29; 12%); 218 (M$^+$−188; 100).

EXAMPLE 3

A—Pharmacological Analysis of Type I (Formula XII) and II (Formula XIII) Imidazole Derivatives

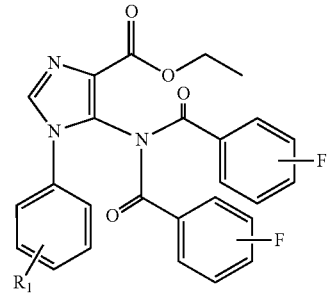

Tipo I (XII)

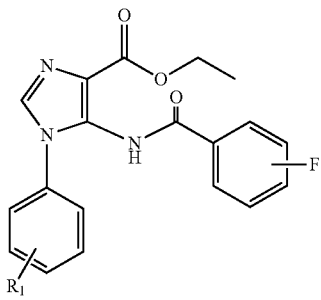

Tipo II (XIII)

A.1—Antimicrobial Activity

The imidazole derivatives with general formula XII and XIII were submitted to a primary biological evaluation, in vitro, regarding the inhibitory activity of *Mycobacterium tuberculosis* H37Rv (ATCC-27294).

The assessment of the minimum inhibitory (MIC) of the substances, that is, the smallest concentration of the compound where the bacterial growth is not observed, was made using the colorimetric method known as MABA (Microplate Alamar Blue Assay). This method consists in an essay performed by the micro dilution in plates, using, as cell growth indicator, the Alamar Blue® indicator pigment, which is a fluorescent/colorimetric indicator with redox property. The oxidized form is blue (non-fluorescent) and indicates the absence of bacterial growth. The reduced form presents a pink color (fluorescent), indicates the proliferation of bacteria.

To perform the essay, sterile micro plates with 96 wells were used in a way that each well presented a total of 200 µL of a mixture composed by the adequate culture mean, of the compound to be tested and of the bacterial suspension. The comparison pattern used was rifampicin, which presents a MIC equal to 1.0 µg/mL.

After 5 incubation days, 15 µL of Alamar Blue® was added to each well and microplates were incubated for more than 24 hours at 37° C. At the end of this period of time, the change of color in each well was observed, and MIC was defined as the smallest concentration of the compound that delimitates the change from blue to pink. Thus, the antimicrobial activity essay of compounds of the type I (Formula XII) and II (Formula XIII) imidazole derivatives and they were able to inhibit the bacterial growth in low concentrations presenting MIC with values 3.0-1.2 µg/mL.

As an example, in table 4, there is a list of the values assessed for MIC, µg/mL, of 146a, 140b, 146c and 146e derivatives.

TABLE 4

Antimicrobial evaluation of the type I (Formula XII) imidazole derivatives

| | 146a | 140b | 146c | 146e |
|---|---|---|---|---|
| MIC | 3.0 µg/mL | 1.2 µg/mL | 3.0 µg/mL | 3.0 µg/mL |

TABLE 5

Antimicrobial evaluation of the type II (Formula XIII) imidazole derivatives

| | 148a | 149b | 149c | 148e |
|---|---|---|---|---|
| MIC | 3.0 µg/mL | 3.0 µg/mL | 3.0 µg/mL | 3.0 µg/mL |

Table 5 shows examples of MIC values assessed for type II (Formula XIII) imidazole derivatives.

A.2—Leishmanicide Activity

The evaluation of the leishmanicide activity of type I (Formula XII) and II (Formula XIII) imidazole derivatives was performed through in vitro essays against promastigote forms of *Leishmania amazonensis*, and after the incubation with compounds, live parasites are counted by fluorescence, thus obtaining as a result the inhibition percentage of the evaluated compounds.

Essays were performed in triplicate using pentamidine as a positive pattern with a 160 μg/mL concentration, determining which compounds evaluated inhibited the parasite in lower concentrations and the percentage higher than the pattern. Table 6 lists the results obtained in the leishmanicide evaluation of derivatives 140a 148a 146a, 149a.

TABLE 6

Evaluation of the leishmanicide activity of type I
(Formula XII) and II (Formula XIII) imidazole derivatives

| Conc. μ/mL | Pentamidine 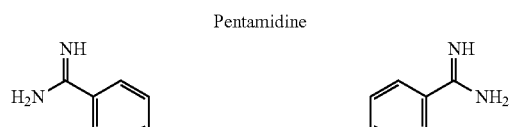 | 140a 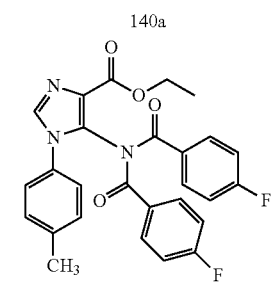 [SMILES: CCOC(=O)c1ncn(-c2ccc(C)cc2)c1N(C(=O)c1ccc(F)cc1)C(=O)c1ccc(F)cc1] |
|---|---|---|
| 320 | | |
| 160 | 53% | |
| 80 | No inhibition | |
| 20 | No inhibition | |
| 10 | No inhibition | 79% |
| 5 | No inhibition | No inhibition |

| Conc. μ/mL | 148a 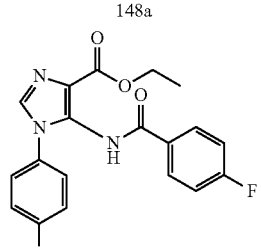 | 146a 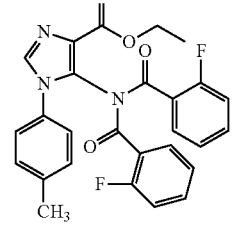 | 149a 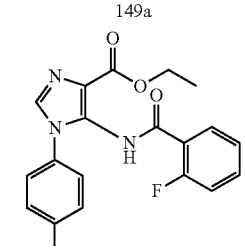 |
|---|---|---|---|
| 320 | | | |
| 160 | | | 93% |
| 80 | | 75% | No inhibition |
| 20 | | No inhibition | No inhibition |
| 10 | 90% | No inhibition | No inhibition |
| 5 | No inhibition | No inhibition | No inhibition |

EXAMPLE 4

Below there is a detailed description of the obtainment of the imidazole compounds substituted twice and substituted that were confirmed by analytical methods represented in FIG. 4.

A—General Method of Obtainment of Type I (Formula XII)—140a-e and 146a-e Imidazole Derivatives

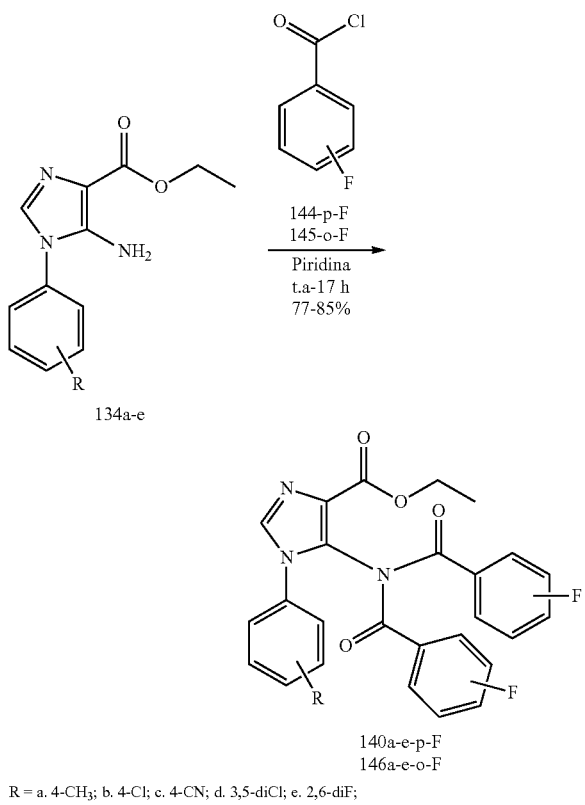

R = a. 4-CH$_3$; b. 4-Cl; c. 4-CN; d. 3,5-diCl; e. 2,6-diF;

In a 25 mL volumetric flask 5.0 mmol of the desired derivative 134a-e was weighed and 5 mL of dry piridine was added. The solution was shaken until complete dissolution of the starting material. Then 15 mmol acid chloride was slowly added. The reaction mixture was shaken, at room temperature, for 17 hours. After this period, 15.0 mmol sodium bicarbonate was added. The suspension was shaken until stopping the effervescency and the solvent was evaporated. The residue obtained was suspended in 40.0 mL of dichloromethane, washed with water (3×20 mL) and with a saturated NaHCO$_3$ (3×15 mL) solution. The organic stage was dried with filtered sodium sulfate and the solvent evaporated. The product obtained was purified by recrystallization with 1:1 ethyl acetate:hexane.

The following products were obtained using this methodology:

A.1—As of the Chloride of 4-Fluorobenzoic (144)

1. Ester ethyl 5-[(bis(4-fluorobenzoic)amino]-1-(4-methylphe-nyl)-1H-imidazole-4-carboxylate (140a)

The derivative 140a was obtained with 81% of output in the form of colorless crystals with fusion point at 203-205° C.
⇒ $^1$H RMN (500.00 MHz; CDCl$_3$/Me$_4$Si) δ (ppm): 1.36 (t, 3H, CH$_3$, J=7.2 Hz); 2.38 (s, 3H, CH$_3$); 4.37 (q, 2H, CH$_2$ J=7.2 Hz); 7.64 (s, 1H, H$_2$); 7.03 (d, 2H, H$_3$, and H$_5$, J=8.4 Hz); 7.20 (d, 2H, H$_2$, and H$_6$, J=8.0 Hz); 6.95 (d, 4H, H$_{3a,3b}$ and H$_{5a, 5b}$, J=8.4 and 2.0 Hz); 7.56 (d, 4H, H$_{2a,2b}$ and H$_{6a,6b}$, J=8.4 and 2.0 Hz);
⇒ $^{13}$C RMN (125.0 MHz) (DMSO$_{d6}$/Me$_4$Si) δ (ppm): 14.4 (CH$_2$CH$_3$); 58.5 (CH$_2$CH$_3$); 115.7 (C$_{3ab-5ab}$; $^2$J$_{CF}$=22.3 Hz); 125.8 (C$_3$, and C$_5$); 126.6 (C$_4$); 127.9 (C$_4$); 129.8 (C$_{1ab}$); 130.4 (C$_2$, and C$_6$); 131.8 (C$_{2ab-6ab}$; $^3$J$_{CF}$=9.4 Hz); 132.9 (C$_2$); 136.2 (C$_1$); 140.6 (C$_5$); 161.5 (NC=O); 165.4 (C$_{4ab}$; $^1$J$_{CF}$=253.8 Hz); 170.7 (OC=O);
⇒ IV (tablet of KBr (1%)) ν (cm$^{-1}$): 1705 (C=O); 1250 (C—F; C—O);
⇒ EM (m/z): 489.47 (M$^{+*}$) 123 (M$^{*+}$−366.47; 100%).

2. Ester ethyl 5-[(bis(4-fluorobenzoic)amino]-1-(4-cyanophe-nyl)-1H-imidazole-4-carboxylate (140b)

The derivative 140b was obtained with 87% of output in the form of colorless crystals with fusion point at 206-208° C.
⇒ $^1$H RMN (400.00 MHz; CDCl$_3$/Me$_4$Si) δ (ppm): 1.36 (t, 3H, CH$_3$, J=8.0 Hz); 4.38 (q, 2H, CH$_2$ J=8.0 Hz); 7.63 (s, 1H, H$_2$); 7.34 (d, 2H, H$_2$, and H$_6$, J=8.0 Hz); 7.74 (d, 2H, H$_3$, and H$_5$, J=8.0 Hz); 6.99 (d, 4H, H$_{3a,3b}$ and H$_{5a, 5b}$, J=8.5 Hz); 7.60 (dq, 4H, H$_{2a,2b}$ and H$_{6a,6b}$, J=8.6; 3.4 and 2.0 Hz);
⇒ $^{13}$C RMN (100.0 MHz) (CDCl$_3$/Me$_4$Si) δ (ppm): 14.3 (CH$_2$CH$_3$); 61.4 (CH$_2$CH$_3$); 117.1 (CN); 114.2 (C$_4$); 115.0 (C$_{3a-5ab}$; $^2$J$_{CF}$=23.0 Hz); 126.5 (C$_2$, and C$_6$); 127.8 (C$_4$); 129.3 (C$_{1ab}$); 131.9 (C$_{2ab-6ab}$; $^3$J$_{CF}$=8.0 Hz); 132.6 (C$_2$); 133.8 (C$_3$, and C$_5$); 135.7 (C$_1$); 136.6 (C$_5$); 165.4 (C$_{4ab}$; $^1$J$_{CF}$=256.0 Hz); 170.0 (OC=O); 161.6 (NC=O);
⇒ IV (tablet of KBr (1%)) ν (cm$^{-1}$): 2230 (CN); 1695 (C=O); 1250 (CF; CO)
⇒ EM (m/z): 500.45 (M$^{*+}$) 123 (M$^{*+}$−377.45; 100%).

3. Ester ethyl 5-[(bis(4-fluorobenzoic)amino]-1-(4-chlorophe-nyl)-1H-imidazole-4-carboxylate (140c)

The derivative 140c was obtained with 87% of output in the form of colorless crystals with fusion point at 225-227° C.
⇒ $^1$H RMN (400.00 MHz; CDCl$_3$/Me$_4$Si) δ (ppm): 1.38 (t, 3H CH$_3$, J=7.2 Hz); 4.38 (q, 2H, CH$_2$ J=7.2 Hz); 7.59 (s, 1H, H$_2$); 7.40 (dd, 2H, H$_2$, and H$_6$, J=8.0 and 2.8 Hz); 7.11 (d, 2H, H$_3$, and H$_5$, J=8.4 and 2.8 Hz); 6.97 (dq, 4H, H$_{3a,3b}$ and H$_{5a, 5b}$, J=8.8, 2.8 and 2.0 Hz); 7.59 (dq, 4H, H$_{2a,2b}$ and H$_{6a,6b}$, J=8.8; 3.6 and 2.0 Hz);
⇒ $^{13}$C RMN (100.0 MHz) (CDCl$_3$/Me$_4$Si) δ (ppm): 140.3 (CH$_2$CH$_3$); 61.2 (CH$_2$CH$_3$); 115.8 (C$_{3ab-5ab}$; $^2$J$_{CF}$=22.3 Hz); 127.3 (C$_2$, and C$_6$); 129.6 (C$_{1ab}$); 130.1 (C$_3$, and C$_5$); 131.5 (C$_2$); 131.8 (C$_{2ab-6ab}$; $^3$J$_{CF}$=8.9 Hz); 131.9 (C$_4$); 131.9 (C$_5$); 136.1 (C$_4$); 136.1 (C$_1$); 161.7 (NC=O); 165.3 (C$_{4ab}$; $^1$J$_{CF}$=254.5 Hz); 170.7 (OC=O);
⇒ IV (tablet of KBr (1%)) ν (cm$^{-1}$): 1700 (C=O); 1242 (CF$_i$; CO);
⇒ EM (m/z): 509.89 (M$^{*+}$) 123 (M$^{*+}$−386.89; 100%).

4. Ester ethyl 5-[(bis(4-fluorobenzoic) amino]-1-(3,5-dichlorophenyl)-1H-imidazole-4-carboxylate (140d)

The derivative 140d was obtained with 78% of output in the form of colorless crystals with fusion point at 140-142.0° C.
⇒ $^1$H RMN (500.00 MHz; CDCl$_3$/Me$_4$Si) δ (ppm): 1.36 (t, 3H CH$_3$, J=7.0 Hz); 4.37 (q, 2H, CH$_2$ J=7.0 Hz); 7.61 (s, 1H, H$_2$); 7.26 (d, 2H, H$_2$, and H$_6$, J=1.5 Hz); 7.61 (t, 1H, H$_4$, J=1.5 Hz); 6.99 (t, 4H, H$_{3a,3b}$ and H$_{5a, 5b}$, J=8.5 Hz); 7.63 (ddd, 4H, H$_{2a,2b}$ and H$_{6a,6b}$, J=7.5; 3.5 and 2.0 Hz);

⇒ $^{13}$C RMN (125.0 MHz) (CDCl$_3$/Me$_4$Si) δ (ppm): 14.3 (CH$_2$CH$_3$); 61.3 (CH$_2$CH$_3$); 115.8 (C$_{3ab\text{-}5ab}$; $^2J_{CF}$=21.8 Hz); 124.5 (C$_{2'}$ and C$_{6'}$); 127.9 (C$_{4'}$); 129.6 (C$_{1ab}$); 130.3 (C$_{4'}$); 131.9 (C$_2$); 131.9 C$_{2ab\text{-}6ab}$; $^3J_{CF}$=7.5 Hz); 132.6 (C$_{1'}$); 135.7 (C$_{3'}$ and C$_{5'}$); 136.3 (C$_5$); 161.6 (NC=O); 165.3 (C$_{4ab}$; $^1J_{CF}$=254.7 Hz); 170.7 (OC=O);

⇒ IV (tablet of KBr (1%)) ν (cm$^{-1}$): 1708 (C=O); 1236 (CF; C—O)

⇒ EM (m/z): 544.33 (M$^{\cdot+}$) 123 (M$^{\cdot+}$−421.33; 100%);

5. Ester ethyl 5-[(bis(4-fluorobenzoic) amino]-1-(2,6-di-fluorophenyl)-1H-imidazole-4-carboxylate (140e)

The derivative 140d was obtained with 77% of output in the form of colorless crystals with fusion point at 178-181.0° C.

⇒ $^1$H RMN (500.00 MHz; CDCl$_3$/Me$_4$Si) δ (ppm): 1.35 (t, 3H CH$_3$, J=7.0 Hz); 4.36 (q, 2H, CH$_2$ J=7.0 Hz); 7.60 (m, 5H, H$_2$, H$_{2a,2b}$ and H$_{6a,6b}$, J=8.5; 5.0 and 3.5 Hz); 7.26 (d, 2H, H$_{3'}$ and H$_{3'}$, J=1.5 Hz); 7.61 (t, 1H, H$_{4'}$, J=1.5 Hz); 6.98 (m, 4H, H$_{3a,3b}$ and H$_{5a,5b}$, J=8.5 Hz).

⇒ $^{13}$C RMN (125.0 MHz) (CDCl$_3$/Me$_4$Si) δ (ppm): 14.3 (CH$_2$CH$_3$); 61.2 (CH$_2$CH$_3$); 112.6 (C$_{3'}$ and C$_{5'}$; $^4J_{CF}$=3.6 Hz); 111.0 (C$_{1'}$); 115.8 (C$_{3ab\text{-}5ab}$; $^2J_{CF}$=22.1 Hz); 127.2 (C$_4$); 129.7 (C$_{1ab}$; $^4J_{CF}$=3.0 Hz); 131.6 (C$_{2ab\text{-}6ab}$; $^3J_{CF}$=9.2 Hz); 131.6 (C$_2$); 132.3 (C$_{4'}$; $^3J_{CF}$=9.3 Hz); 137.2 (C$_5$); 157.8 (C$_{2'}$ and C$_{6'}$; $^1J_{CF}$=256.0 Hz); 161.6 (NC=O); 165.2 (C$_{4ab}$; $^1J_{CF}$=254.0 Hz); 169.5 (OC=O);

⇒ IV (tablet of KBr (1%)) ν (cm$^{-1}$): 1726; 1694 (C=O); 1236 (CF; CO)

⇒ EM (m/z): 511.12 (M$^{\cdot+}$); 123 (M$^{\cdot+}$−388.12; 100%)

A.2—As of the chloride of 2-fluorobenzoic (145)

1. Ester ethyl 5-[(bis(2-fluorobenzoic) amino]-1-(4-methylphenyl)-1H-imidazole-4-carboxylate (146a)

The derivative 146a was obtained with 83% of output in the form of transparent crystals with fusion point at 176.5° C.

⇒ $^1$H RMN (500.00 MHz; CDCl$_3$/Me$_4$Si) δ (ppm): 1.35 (t, 3H, CH$_3$, J=10.0 Hz); 3.83 (s, 3H, CH$_3$); 4.38 (q, 2H, CH$_2$ J=10.0 Hz); 6.86 (t, 2H, H$_{3a,3b}$; J=5.0 Hz); 6.95 (d, 2H, H$_{3'}$ and H$_{5'}$, J=10.0 Hz); 7.18 (d, 2H, H$_{2'}$ and H$_{6'}$, J=10.0 Hz); 7.24 (t, 2H, H$_{5a,2b}$; J=5.0 Hz); 7.33 (d, 2H, H$_{4a,b}$; J=5.0 Hz); 7.50 (sl, 2H, H$_{6a,b}$); 7.61 (s, 1H, H$_2$);

⇒ $^{13}$C RMN (125.0 MHz) (DMSO$_{d6}$/Me$_4$Si) δ (ppm): 14.3 (CH$_2$CH$_3$); 60.9 (CH$_2$CH$_3$); 21.1 (CH$_3$); 114.8 (C$_{2'}$ and C$_{6'}$); 116.1 (C$_{3ab}$; $^2J_{CF}$=21.5 Hz); 122.4 (C$_{1ab}$; $^2J_{CF}$=11.2 Hz); 124.0 (C$_{5ab}$; $^4J_{CF}$=2.5 Hz); 127.3 (C$_{3'}$ and C$_{5'}$); 128.0 (C$_4$); 128.6 (C$_{4'}$); 130.6 (C$_{6ab}$); 131.2 (C$_5$); 133.2 (C$_{1'}$); 134.1 (C$_{4ab}$ $^3J_{CF}$=8.7 Hz); 136.7 (C$_2$); 159.5 (C$_{2ab}$; $^1J_{CF}$=255.0 Hz); 160.6 (NC=O); 167.1 (OC=O);

⇒ IV (tablet of KBr (1%)) ν (cm$^{-1}$): 1692 (C=O); 1257 (CF; C—O);

⇒ EM (m/z): 489.47 (M$^{\cdot+}$) 123 (M$^{\cdot+}$−366.47; 100%);

2. Ester ethyl 5-[(bis(2-fluorobenzoic)amino]-1-(4-chloridephe-nyl)-1H-imidazole-4-carboxylate (146c)

The derivative 146c was obtained with 80% of output in the form of transparent crystals with fusion point at 199-200.0° C.

⇒ $^1$H RMN (400.00 MHz; CDCl$_3$/Me$_4$Si) δ (ppm): 1.35 (t, 3H, CH$_3$, J=7.2 Hz); 4.38 (q, 2H, CH$_2$ J=7.2 Hz); 6.85 (t, 2H, H$_{3a,3b}$; J=9.6 Hz); 7.06 (t, 2H, H$_{5a,b}$; J=7.6 Hz); 7.24 (d, 2H, H$_{2'}$ and H$_{6'}$, J=8.4 Hz); 7.33 (dq, 2H, H$_{4a,b}$; J=7.2 and 4.0 Hz); 7.45 (d, 2H, H$_{3'}$ and H$_{5'}$, J=8.4 Hz); 7.51 (t, 2H, H$_{6ab}$; J=7.2 and 6.4 Hz); 7.74 (s, 1H, H$_2$);

⇒ $^{13}$C RMN (100.0 MHz) (DMSO$_{d6}$/Me$_4$Si) δ (ppm): 14.2 (CH$_2$CH$_3$); 61.2 (CH$_2$CH$_3$); 127.3 (C$_{2'}$ and C$_{6'}$); 116.1 (C$_{3ab}$; $^2J_{CF}$=21.7 Hz); 122.2 (C$_{1ab}$; $^2J$=12.1 Hz); 124.2 (C$_{5ab}$); 128.1 (C$_4$); 128.6 (C$_{4'}$); 130.8 (C$_{3'}$ and C$_{5'}$); 130.1 (C$_{6ab}$); 131.2 (C$_5$); 131.7 (C$_{1'}$); 134.4 (C$_{4ab}$ $^3J_{CF}$=8.4 Hz); 136.3 (C$_2$); 159.5 (C$_{2ab}$; $^1J_{CF}$=243.1 Hz); 160.7 (NC=O); 166.9 (OC=O);

⇒ IV (tablet of KBr (1%)) ν (cm$^{-1}$): 1719 (C=O); 1233 (CF; CO);

⇒ EM (m/z): 509.89 (M$^{\cdot+}$) 123 (M$^{\cdot+}$−386.89; 100%);

3. Ester ethyl 5-[(bis(2-fluorobenzoic)amino]-1-(3,5-dichloride-phenyl)-1H-imidazole-4-carboxylate (146d)

The derivative 146d was obtained with 83% of output in the form of transparent crystals with fusion point at 140-142.0° C.

⇒ $^1$H RMN (500.00 MHz; CDCl$_3$/Me$_4$Si) δ (ppm): 1.34 (t, 3H, CH$_3$, J=7.2 Hz); 4.38 (q, 2H, CH$_2$ J=7.2 Hz); 6.87 (t, 2H, H$_{3a,3b}$; J=9.6 Hz); 7.09 (t, 2H, H$_{5a,b}$; J=7.6 Hz); 7.24 (d, 2H, H$_{2'}$ and H$_{6'}$, J=1.6 Hz); 7.35 (dq, 2H, H$_{4a,b}$; J=7.2 and 4.8 Hz); 7.45 (d, 1H, H$_{4'}$; J=1.6 Hz); 7.58 (t, 2H, H$_{6ab}$, J=7.5 and 6.5 Hz); 7.66 (s, 1H, H$_2$);

⇒ $^{13}$C RMN (125.0 MHz) (DMSO$_{d6}$/Me$_4$Si) δ (ppm): 14.2 (CH$_2$CH$_3$); 61.1 (CH$_2$CH$_3$); 124.4 (C$_{2'}$ and C$_{6'}$); 116.0 (C$_{3ab}$; $^2J_{CF}$=22.3 Hz); 122.1 (C$_{1ab}$; $^2J_{CF}$=11.6 Hz); 124.2 (C$_{5ab}$); 128.9 (C4); 130.1 (C$_{4'}$); 136.0 (C$_{3'}$ and C$_{5'}$); 130.9 (C$_{6ab}$); 131.0 (C5); 131.7 (C$_{1'}$); 134.9 (C$_{4ab}$ $^3J_{CF}$=10.0 Hz); 136.3 (C$_2$); 159.7 (C$_{2ab}$; $^1J_{CF}$=260.8 Hz); 160.6 (NC=O); 166.8 (OC=O);

⇒ IV (tablet of KBr (1%)) ν (cm$^{-1}$): 1705 (C=O); 1239 (CF; CO);

⇒ EM (m/z): 544.33 (M$^{\cdot+}$) 123 (M$^{\cdot+}$−421.45; 100%);

4. Ester ethyl 5-[(bis(2-fluorobenzoic) amino]-1-(2,6-difluoro-phenyl)-1H-imidazole-4-carboxylate (146e)

The derivative 146e was obtained with 80% of output in the form of transparent crystals with fusion point at 178-181.0° C.

⇒ $^1$H RMN (500.00 MHz; CDCl$_3$/Me$_4$Si) δ (ppm): 1.36 (t, 3H CH$_3$, J=7.0 Hz); 4.40 (q, 2H, CH$_2$ J=7.0 Hz); 7.06 (t, 4H, H$_{3'}$ and H$_{5'}$, J=8.0 Hz); 7.06 (t, 4H, H$_{5ab}$, J=8.0 Hz); 7.34 (dq, 2H, H$_{4ab}$; J=12.0, 5.5 and 1.5 Hz); 7.46 (dq, 1H, H$_{4'}$, J=6.0 and 2.5 Hz); 7.59 (d, 2H, H$_{6ab}$; J=6.5 Hz); 7.61 (s, 1H, H$_2$); 7.85 (t, 2H, H$_{3ab}$; J=10.0 Hz);

⇒ $^{13}$C RMN (125.0 MHz) (CDCl$_3$/Me$_4$Si) δ (ppm): 14.2 (CH$_2$CH$_3$); 61.1 (CH$_2$CH$_3$); 111.2 (C$_{1'}$; $^2J_{CF}$=15.0 Hz); 115.8 (C$_{3ab}$; $^2J_{CF}$=22.1 Hz); 122.6 (C$_{3'}$ and C$_{5'}$; $^3J_{CF}$=19.5 Hz); 122.3 (C$_{1ab}$; $^3J_{CF}$=11.8 Hz); 124.2 (C$_{5ab}$); 128.6 (C$_4$); 130.7 (C$_5$); 130.7 (C$_{6ab}$); 132.3 (C$_{4'}$; $^3J_{CF}$=9.9 Hz); 134.9 (C$_{4ab}$; $^3J_{CF}$=10.0 Hz); 137.5 (C$_2$); 157.8 (C$_{2ab}$; $^1J_{CF}$=255.3 Hz); 159.5 (C$_{2'}$ and C$_{6'}$; $^1J_{CF}$=255.0 Hz); 160.6 (NC=O); 166.8 (OC=O);

⇒ IV (tablet of KBr (1%)) ν (cm$^{-1}$): 1705 (C=O); 1253 (C—F; C—O);

⇒ EM (m/z): 511.12 (M$^{\cdot+}$); 123 (M$^{\cdot+}$−388.12; 100%).

B—General Method of Obtainment of Type II (Formula XIII) 148a-e 149a-e Imidazole Derivatives

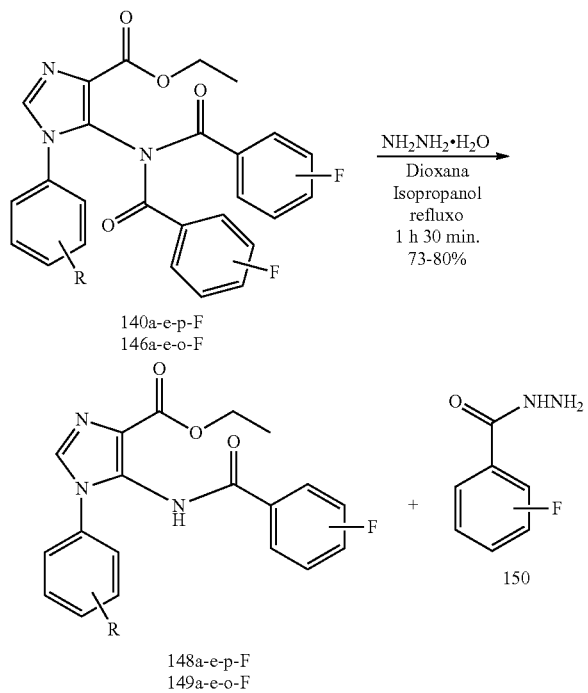

140a-e-p-F
146a-e-o-F 148a-e-p-F
149a-e-o-F

R = a. 4-CH₃; b. 4-CN c. 4-Cl; d. 3,5-diCl e. 2,5-diF

In a 50 mL balloon 5 mmol of the desired twice substituted derivative, 10 mL of dioxane and 2 mL of 2-propanol were added. The solution was shaken during some minutes and 5 mmol of 60% hidrazine hydrate were added, drip by drip, during some minutes. The reaction mixture was reflowed for 1 h and 30 min and observing the consume of the starting material, by c.c.f, using ethyl:hexane 7:3 acetate. The solvent was evaporated and the residue obtained by column chromatography in silica gel using ethyl:hexane 7:3 acetate as eluant.

The following products were obtained using this methodology:

1. Ester ethyl 5-[(4-fluorobenzoic)amino]-1-(4-methylphenyl)-1H-imidazole-4-carboxylate (148a)

The derivative 148a was obtained with 74% of output in the form of crystals shaped as colorless needles with fusion point at 183-185.0° C.

⇒ $^1$H RMN (500.00 MHz; CDCl$_3$/Me$_4$Si) δ (ppm): 1.34 (t, 3H, CH$_3$, J=7.0 Hz); 2.36 (s, 3H, CH$_3$); 4.34 (q, 2H, CH$_2$ J=7.0 Hz); 7.09 (t, 2H, H$_{3a}$ and H$_{5a}$; J=8.5 Hz); 7.23 (d, 2H, H$_{3'}$ and H$_{5'}$, J=8.5 Hz); 7.24 (dq, 2H, H$_{2a}$ and H$_{6a}$; J=8.5; 5.0 and 3.5 Hz); 7.28 (d, 2H, H$_{2'}$ and H$_{6'}$, J=8.5 Hz); 7.59 (s, 1H, H$_2$); 9.15 (s, H, NH);

⇒ $^{13}$C RMN (125.0 MHz) (DMSO$_{d6}$/Me$_4$Si) δ (ppm): 14.3 (CH$_2$CH$_3$); 60.9 (CH$_2$CH$_3$); 21.1 (CH$_3$); 115.7 (C$_{3ab-5ab}$; $^2$J$_{CF}$=22.3 Hz); 122.7 (C$_4$); 123.8 (C$_{2'}$ and C$_{6'}$); 128.9 (C$_{1ab}$; $^4$J$_{CF}$=3.0 Hz); 130.2 (C$_{3'}$ and C$_{5'}$); 130.2 (C$_{2ab-6ab}$; $^3$J$_{CF}$=8.8 Hz); 133.3 (C$_5$); 133.8 (C$_1$); 135.5 (C$_2$); 138.9 (C$_4$); 163.7 (NC=O); 164.8 (OC=O); 165.4 (C$_{4ab'}$; $^1$J$_{CF}$=252.5 Hz);

⇒ IV (tablet of KBr (1%)) ν (cm$^{-1}$): 3187 (NH); 1711, 1686 (C=O); 1250 (C—F; C—O)

⇒ EM (m/z): 367.37 (M$^{•+}$) 123 (M$^{•+}$–244.37; 100%)

2. Ester 1-(4-cyanophenyl)-5-[(4-fluorobenzoic) amino]-1H-imidazole-4-carboxylate de ethyl (148b)

The derivative 148b was obtained with 73% of output in the form of colorless crystals with fusion point at 223-224.0° C.

⇒ $^1$H RMN (400.00 MHz; CDCl$_3$/Me$_4$Si) δ (ppm): 1.40 (t, 3H, CH$_3$, J=7.0 Hz); 4.40 (q, 2H, CH$_2$ J=7.0 Hz); 7.27 (s, 1H, H$_2$); 7.14 (t, 2H, H$_{3a}$e H$_{5a}$ J=8.5 Hz); 7.50 (d, 2H, H$_{2'}$ and H$_{6'}$, J=8.5 Hz); 7.78 (d, 2H, H$_{3'}$ and H$_{5'}$, J=8.5 Hz); 7.88 (dq, 2H, H$_{2a}$ and H$_{6a}$; J=8.6; 5.1 and 3.4 Hz); 9.51 (s, H, NH);

⇒ $^{13}$C RMN (100.0 MHz) (CDCl$_3$/Me$_4$Si) δ (ppm): 14.3 (CH$_2$CH$_3$); 61.4 (CH$_2$CH$_3$); 112.8 (C$_{4'}$); 115.8 (CN); 116.1 (C$_{3ab-5ab}$; $^2$J$_{CF}$=22.0 Hz); 122.0 (C$_4$); 124.4 (C$_{2'}$ and C$_{6'}$); 129.8 (C$_{1ab}$; $^4$J$_{CF}$=3.2 Hz); 130.2 (C$_{2ab-6ab}$; $^3$J$_{CF}$=9.1 Hz); 133.8 (C$_{3'}$ and C$_{5'}$); 134.1 (C$_5$); 134.6 (C$_2$); 139.6 (C$_1$); 163.5 (NC=O); 164.6 (OC=O); 165.5 (C$_{4ab}$; $^1$J$_{CF}$=287.5 Hz);

⇒ IV (tablet of KBr (1%)) ν (cm$^{-1}$): 3246 (NH); 2227 (CN); 1716 and 1661 (C=O);

⇒ EM (m/z): 378.36 (M$^{•+}$) 123 (M$^{•+}$–255.45; 100%);

3. Ester ethyl 1-(4-chlorophenyl)-5-[(4-fluorobenzoic)amino]-1H-imidazole-4-carboxylate (148c)

The derivative 148c was obtained with 75% of output in the form of crystals with fusion point at 174-177° C.

⇒ $^1$H RMN (400.00 MHz; CDCl$_3$/Me$_4$Si) δ (ppm): 1.38 (t, 3H CH$_3$, J=7.2 Hz); 4.38 (q, 2H, CH$_2$ J=7.2 Hz); 7.61 (s, 1H, H$_2$); 7.37 (d, 2H, H$_{2'}$ and H$_{6'}$, J=8.8 Hz); 7.43 (d, 2H, H$_{3'}$ and H$_{5'}$, J=8.4 Hz); 7.13 (t, 2H, H$_{3a}$ and H$_{5a}$ J=8.4 Hz); 7.87 (dq, 2H, H$_{2a}$ and H$_{6a}$; J=8.4; 5.1 and 3.4 Hz); 9.21 (s, 1H, NH);

⇒ $^{13}$C RMN (100.0 MHz) (CDCl$_3$/Me$_4$Si) δ (ppm): 14.2 (CH$_2$CH$_3$); 61.1 (CH$_2$CH$_3$); 116.8 (C$_{3a-5a}$; $^2$J$_{CF}$=22.0 Hz); 125.3 (C$_{2'}$ and C$_{6'}$); 128.6 (C$_{1ab}$); 129.9 (C$_{3'}$ and C$_{5'}$); 135.1 (C$_2$); 130.2 (C$_{2a-6a}$; $^3$J$_{CF}$=9.0 Hz); 122.2 (C$_4$); 134.9 (C$_5$); 134.9 (C$_{4'}$); 134.3 (C$_{1'}$); 164.5 (NC=O); 165.5 (C$_{4a}$; $^1$J$_{CF}$=253.0 Hz); 164.5 (OC=O);

⇒ IV (tablet of KBr (1%)) ν (cm$^{-1}$): 3290 (NH); 1700 and 1664 (C=O)

⇒ EM (m/z): 387.79 (M$^{•+}$) 123 (M$^{•+}$–264.89; 100%);

4. Ester ethyl 1-(3,5-dichlorophenyl)-5-[(4-fluorobenzoic) amino]-1H-imidazole-4-carboxylate (148d)

The derivative 148d was obtained with 77% of output in the form of crystals with fusion point at 141-142.0° C.

⇒ $^1$H RMN (500.00 MHz; CDCl$_3$/Me$_4$Si) δ (ppm): 1.37 (t, 3H CH$_3$, J=7.0 Hz); 4.38 (q, 2H, CH$_2$ J=7.0 Hz); 7.15 (t, 2H, H$_{3a}$ and H$_{5a}$ J=8.5 Hz); 7.36 (d, 2H, H$_{2'}$ and H$_{6'}$, J=2.0 Hz); 7.40 (d, 1H, H$_{4'}$, J=2.0 Hz); 7.60 (s, 1H, H$_2$); 7.90 (ddd, 2H, H$_{2a}$ and H$_{6a}$, J=8.5; 5.0 and 3.5 Hz); 9.39 (s, 1H, NH);

⇒ $^{13}$C RMN (125.0 MHz) (CDCl$_3$/Me$_4$Si) δ (ppm): 14.3 (CH$_2$CH$_3$); 61.2 (CH$_2$CH$_3$); 116.1 (C$_{3a-5a}$, $^2$J$_{CF}$=220.0 Hz); 122.3 (C$_4$); 122.5 (C$_{2'}$ and C$_{6'}$); 128.5 (C$_{1ab}$; $^4$J$_{CF}$=2.8 Hz); 129.1 (C$_{4'}$); 130.2 (C$_{2a-6a}$; $^3$J$_{CF}$=9.25 Hz); 134.0 (C$_5$); 134.8 (C$_{3'}$ and C$_{5'}$); 136.0 (C$_2$); 137.6 (C$_{1'}$); 163.6 (NC=O); 164.7 (OC=O); 165.6 (C$_{4ab}$; $^1$J$_{CF}$=253.1 Hz);

⇒ IV (tablet of KBr (1%)) ν (cm$^{-1}$): 3290 (NH); 1708 and 1678 (C=O);

⇒ EM (m/z): 422.24 (M$^{•+}$) 123 (M$^{•+}$–299.24; 100%).

5. Ester ethyl 1-(2,6-difluorophenyl)-5-[(4-fluorobenzoic) amino]-1H-imidazole-4-carboxylate (148e)

The derivative 148e was obtained with 77% of output in the form of crystals with fusion point at 179.0° C.

⇒ $^1$H RMN (500.00 MHz; CDCl$_3$/Me$_4$Si) δ (ppm): 1.41 (t, 3H CH$_3$, J=7.0 Hz); 4.41 (q, 2H, CH$_2$ J=7.0 Hz); 7.84 (dq; 2H; H$_{2a}$ and H$_{6a}$; J=8.5; 5.1 and 3.4 Hz); 7.09 (m, 4H, H$_{3'}$ and H$_{5'}$.

J=8.5 and 3.0 Hz); 7.40 (m, 1H, H$_{4'}$, J=8.5, 6.0 and 2.5 Hz); 7.09 (m, 4H, H$_{3a}$ and H$_{5a}$; J=8.5 Hz); 7.54 (s, 1H, H$_2$); 9.48 (s, 1H, NH);

⇒ $^{13}$C RMN (125.0 MHz) (CDCl$_3$/Me$_4$Si) δ (ppm): 14.3 (CH$_2$CH$_3$); 61.2 (CH$_2$CH$_3$); 112.5 (C$_3$, and C$_5$; $^2J_{CF}$=22.0 Hz; $^4J_{CF}$=3.6 Hz); 114.2 (C$_1$; $^2J_{CF}$=16.0 Hz); 116.0 (C$_{3a-5a}$; $^2J_{CF}$=22.1 Hz); 127.2 (C$_4$); 129.7 (C$_{1a}$; $^4J_{CF}$=2.8 Hz); 130.2 (C$_{2a-6a}$; $^3J_{CF}$=9.25 Hz); 130.8 (C$_4$; $^3J_{CF}$=9.6 Hz); 131.6 (C$_2$); 137.2 (C$_5$); 157.2 (C$_{2'}$ and C$_{6'}$; $^1J_{CF}$=250.0 Hz and $^3J_{CF}$=3.0 Hz); 163.9 (NC=O); 164.0 (OC=O); 165.5 (C$_{4a}$; $^1J_{CF}$=252.6 Hz);

⇒ IV (tablet of KBr (1%)) ν (cm$^{-1}$): 3297 (NH); 1718 (C=O);

⇒ EM (m/z): 389.33 (M$^{\cdot+}$); 123 (M$^{\cdot+}$−266.33; 100%);

6. Ester ethyl 5-[(2-fluorobenzoic)amino]-1-(4-methylphenyl)-1H-imidazole-4-carboxylate (149a)

The derivative 149a was obtained with 76% of output in the form of crystals with fusion point at 166.0-167.0° C.

⇒ $^1$H RMN (500.00 MHz; CDCl$_3$/Me$_4$Si) δ (ppm): 1.37 (t, 3H, CH$_3$, J=7.0 Hz); 2.37 (s, 3H, CH$_3$); 4.39 (q, 2H, CH$_2$ J=7.0 Hz); 7.24 (m, 2H, H$_{3a\ and\ 5a}$; J=8.4 and 4.9 Hz); 7.25 (d, 2H, H$_3$, and H$_5$, J=8.2 Hz); 7.30 (d, 2H, H$_2$, and H$_6$, J=8.2 Hz); 7.55 (d, 1H, H$_{4a}$; J=7.4 and 5.8 Hz); 7.91 (t, 1H, H$_{6a}$; J=7.5 Hz); 7.65 (s, 1H, H$_2$); 9.21 (d, 1H, NH, J=13.5 Hz);

⇒ $^{13}$C RMN (125.0 MHz) (DMSO$_{d6}$/Me$_4$Si) δ (ppm): 14.3(CH$_2$CH$_3$); 60.9 (CH$_2$CH$_3$); 21.1 (CH$_3$); 116.5 (C$_{3a}$; $^2J_{CF}$=3.7 Hz); 119.1 (C$_{1a}$; $^2J_{CF}$=11.2 Hz); 123.2 (C$_4$); 123.8 (C$_{2'}$ and C$_{6'}$); 124.9 (C$_{5a}$; $^4J_{CF}$=3.1 Hz); 130.2 (C$_{3'}$ and C$_{5'}$); 132.2 (C$_{6a}$); 132.5 (C$_5$); 133.2 (C$_{1'}$); 134.5 (C$_{4a}$; $^3J_{CF}$=9.1 Hz); 135.6 (C$_2$); 138.9 (C$_{4'}$); 160.8 (C$_{2a}$; $^1J_{CF}$=247.5 Hz); 161.8 (NC=O); 163.0 (OC=O);

⇒ IV (tablet of KBr (1%)) ν (cm$^{-1}$): 3235 (NH); 1714 and 1683 (C=O);

⇒ EM (m/z): 367.37 (M$^{\cdot+}$) 123 (M$^{\cdot+}$−244.37; 100%).

7. Ester ethyl 1-(4-cyanophenyl)-5-[(2-fluorobenzoic)amino]-1H-imidazole-4-carboxylate (149b)

The derivative 149a was obtained with 80% of output in the form of crystals with fusion point at 171.0-172.0° C.

⇒ $^1$H RMN (500.00 MHz; CDCl$_3$/Me$_4$Si) δ (ppm): 1.41 (t, 3H, CH$_3$, J=10.0 Hz); 4.42 (q, 2H, CH$_2$ J=10.0 Hz); 7.24 (m, 2H, H$_{3a\ and\ 5a}$; J=10.0 and 5.0 Hz); 7.56 (m, 1H, H$_{4a}$; J=5.0 Hz); 7.58 (d, 2H, H$_2$, and H$_6$, J=10.0 Hz); 7.68 (s, 1H, H$_2$); 7.79 (d, 2H, H$_3$, and H$_5$, J=8.2 Hz); 7.85 (t, 1H, H$_{6a}$ J=10.0 Hz); 9.60 (d, 1H, NH, J=15.0 Hz);

⇒ $^{13}$C RMN (125.0 MHz) (DMSO$_{d6}$/Me$_4$Si) δ (ppm): 14.3 (CH$_2$CH$_3$); 61.7 (CH$_2$CH$_3$); 112.7 (C$_{4'}$); 117.7 (CN); 116.5 (C$_{3a}$; $^2J_{CF}$=23.7 Hz); 119.1 (C$_{1a}$; $^2J_{CF}$=11.2 Hz); 123.0 (C$_4$); 124.4 (C$_{2'}$ and C$_{6'}$); 125.1 (C$_{5a}$; $^4J_{CF}$=2.5 Hz); 132.1 (C$_{6a}$); 132.8 (C$_5$); 133.8 (C$_{3'}$ and C$_{5'}$); 134.7 (C$_2$); 135.0 (C$_{4a}$; $^3J_{CF}$=10.0 Hz); 139.8 (C$_{1'}$); 160.9 (C$_{2a}$; $^1J_{CF}$=248.7 Hz); 161.6 (NC=O, $^3J_{CF}$=2.5 Hz); 163.0 (OC=O);

⇒ IV (tablet of KBr (1%)) ν (cm$^{-1}$: 3244 (NH); 2227 (CN); 1716 and 1661 (C=O);

⇒ EM (m/z): 378.36 (M$^{\cdot+}$); 123 (M$^{\cdot+}$−255.36; 100%).

8. Ester ethyl 1-(4-chlorophenyl)-5-[(2-fluorobenzoic)amino]-1H-imidazole-4-carboxylate (149c)

The derivative 149c was obtained with 74% of output in the form of crystals with fusion point at 156.0-157.0° C.

⇒ $^1$H RMN (400.00 MHz; CDCl$_3$/Me$_4$Si) δ (ppm): 1.38 (t, 3H, CH$_3$, J=10.0 Hz); 4.39 (q, 2H, CH$_2$ J=10.0 Hz); 7.22 (m, 2H, H$_{3a\ and\ 5a}$; J=8.4; 6.4 and 3.6 Hz); 7.37 (dd, 2H, H$_2$, and H$_6$, J=8.8 and 2.0 Hz); 7.43 (dd, 2H, H$_3$, and H$_5$, J=9.2 and 2.4 Hz); 7.54 (dq, 1H, H$_{4a}$; J=6.4 and 3.6 Hz); 7.64 (s, 1H, H$_2$); 7.88 (t, 1H, H$_{6a}$ J=8.0 and 2.0 Hz); 9.27 (d, 1H, NH, J=15.0 Hz);

⇒ $^{13}$C RMN (100.0 MHz) (DMSO$_{d6}$/Me$_4$Si) δ (ppm): 14.3 (CH$_2$CH$_3$); 61.0 (CH$_2$CH$_3$); 116.4 (C$_{3a}$; $^2$H$_{CF}$=24.5 Hz); 119.4 (C$_{1a}$; $^2J_{CF}$=11.5 Hz); 123.0 (C$_4$); 125.0 (C$_{5a}$; $^4J_{CF}$=2.7 Hz); 125.4 (C$_{2'}$ and C$_{6'}$); 129.9 (C$_{3'}$ and C$_{5'}$); 132.1 (C$_{6a}$); 132.8 (C$_5$); 134.5 (C$_{4a}$; $^3J_{CF}$=10.0 Hz); 134.7 (C$_2$); 134.8 (C$_{4'}$); 139.8 (C$_{1'}$); 160.9 (C$_{2a}$; $^1J_{CF}$=248.4 Hz); 161.8 (NC=O, $^3J_{CF}$=3.9 Hz); 162.9 (OC=O);

⇒ IV (tablet of KBr (1%)) ν (cm$^{-1}$): 3266 (NH) 1770; 1664 (C=O);

⇒ EM (m/z): 387.79 (M$^{\cdot+}$); 123 (M$^{\cdot+}$−264.79; 100%).

9. Ester ethyl 1-(3,5-dichlorophenyl)-5-[(2-fluoroben-zoic)amino]-1H-imidazole-4-carboxylate (149d)

The derivative 149d was obtained with 80% of output in the form of crystals with fusion point at 76.0-77.0° C.

⇒ $^1$H RMN (500.00 MHz; CDCl$_3$/Me$_4$Si) δ (ppm): 1.40 (t, 3H, CH$_3$, J=7.5 Hz); 4.40 (q, 2H, CH$_2$ J=7.0 Hz); 7.24 (m, 2H, H$_{3a\ and\ 5a}$; J=8.5 and 3.5 Hz); 7.36 (d, 2H, H$_2$, and H$_6$, J=2.0 Hz); 7.41 (d, 2H, H$_4$, J=2.0 Hz); 7.56 (dq, 1H, H$_{4a}$; J=7.5 and 1.5 Hz); 7.65 (s, 1H, H$_2$); 7.89 (t, 1H, H$_{6a}$ J=7.5 and 6.5 Hz); 9.44 (d, 1H, NH, J=13.0 Hz);

⇒ $^{13}$C RMN (125.0 MHz) (DMSO$_{d6}$/Me$_4$Si) δ (ppm): 14.3 (CH$_2$CH$_3$); 61.7 (CH$_2$CH$_3$); 116.4 (C$_{3a}$; $^2J_{CF}$=23.7 Hz); 119.3 (C$_{1a}$; $^2J_{CF}$=11.2 Hz); 123.0 (C$_4$); 122.5 (C$_{2'}$ and C$_{6'}$); 125.1 (C$_{5a}$; $^4J_{CF}$=2.5 Hz); 129.0 (C$_{4'}$); 135.1 (C$_{3'}$ and C$_{5'}$); 132.0 (C$_{6a}$); 132.6 (C$_5$); 134.7 (C$_2$); 134.8 (C$_{4a}$; $^3J_{CF}$=8.7 Hz); 137.6 (C$_{1'}$); 160.9 (C$_{2a}$; $^1J_{CF}$=247.5 Hz); 161.9 (NC=O); 162.9 (OC=O);

⇒ IV (tablet of KBr (1%)) ν (cm$^{-1}$): 3549 (NH); 1725 and 1686 (C=O);

⇒ EM (m/z): 422.24 (M$^{\cdot+}$); 123 (M$^{\cdot+}$−299.24; 100%).

10. Ester ethyl 1-(2,6-difluorophenyl)-5-[(2-fluoroben-zoic)amino]-1H-imidazole-4-carboxylate (149e)

The derivative 149e was obtained with 75% of output in the form of transparent crystals with fusion point at 184.0° C.

⇒ $^1$H RMN (500.00 MHz; CDCl$_3$/Me$_4$Si) δ (ppm): 1.41 (t, 3H CH$_3$, J=10.0 Hz); 4.42 (q, 2H, CH$_2$ J=10.0 Hz); 7.85 (t; 1H; H$_{6a}$; J=10.0 and 5.0 Hz); 7.08 (t, 2H, H$_3$, and H$_5$, J=10.0 and 5.0 Hz); 7.53 (dq, 1H, H$_4$, J=10.0 and 5.0 Hz); 7.19 (m, 2H, H$_{3a}$ and H$_{5a}$; J=10.0 and 5.0 Hz); 7.40 (dq; 1H; H$_{4a}$; J=12.0, 5.5 and 1.5 Hz); 7.57 (s, 1H, H$_2$); 9.57 (s, 1H, NH);

⇒ $^{13}$C RMN (125.0 MHz) (CDCl$_3$/Me$_4$Si) δ (ppm): 14.3 (CH$_2$CH$_3$); 61.0 (CH$_2$CH$_3$); 114.0 (C$_1$; $^2J_{CF}$=16.0 Hz); 116.0 (C$_{3a}$; $^2J_{CF}$=23.7 Hz); 119.3 (C$_{1a}$; $^2J_{CF}$=11.2 Hz); 121.7 (C$_4$); 122.6 (C$_{3'}$ and C$_{5'}$; $^3J_{CF}$=19.5 Hz); 124.0 (C$_{5a}$; $^4J_{CF}$=2.5 Hz); 130.7 (C$_{4'}$; $^3J_{CF}$=10.0 Hz); 132.0 (C$_{6a}$); 134.7 (C$_{4a}$; $^3J_{CF}$=8.7 Hz); 134.4 (C$_5$); 135.8 (C$_2$); 157.2 (C$_{2a}$; $^1J_{CF}$=255.3 and $^1J_{CF}$=3.7 Hz); 160.8 (C$_{2'}$ and C$_{6'}$; $^1J_{CF}$=247.5 Hz); 161.3 (NC=O); 163.1 (OC=O);

⇒ IV (tablet of KBr (1%)) ν (cm$^{-1}$): 3167 (NH); 1688 (C=O);

⇒ EM (m/z): 389.33 (M$^{\cdot+}$); 123 (M$^{\cdot+}$−266.33; 100%).

The invention hereby described, as the aspects approached must be considered as one of the possible concretizations. However, it must be clear that the invention is not limited to these concretizations and that those with technical capacity shall notice that any particular characteristics introduced to it should be only understood as something that was described in order to facilitate the understanding and cannot be made without departing from the inventive concept described. The limiting characteristics of this invention are related to the claims that are part of this report.

The invention claimed is:

1. AZOLE COMPOUNDS wherein the compounds 1,2,3-triazole, or one of its salts, is represented by the general formula VIII:

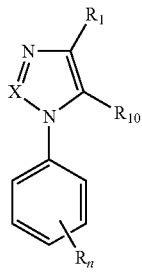

(VIII)

where:
  where X is "N" and the radicals of the triazole ring are represented by:
    $R_1=CF_2R_6$;
    $R_6=R_{10}$=alkyl; and
  where radical $R_n$ can be located in any one or in more than one of the carbon atoms of the aromatic ring, and is represented by a halogen.

2. AZOLE COMPOUNDS according to claim 1 wherein the compounds 1,2,3-triazole are selected among:
  1-(3-chlorophenyl)-4-difluoromethyl -1H-1,2,3-triazole; and
  1-(3,5-dichlorophenyl)-4-difluoromethyl-1H-1,2,3-triazole;
  or one of their salts.

3. AZOLE COMPOUNDS according to claim 1 wherein the compounds 1,2,3-triazole are selected among:
  (AND)-4-chloride-N-((1-(4-chlorophenyl)-1H-1,2,3-triazole-4-il)methylene)benzenamine; and,
  (AND)-4-bromo-N-((1-(4-bromophenyl)-1H-1,2,3-triazole-4-il)methylene)benzenamine, or one of their salts.

4. A PHARMACEUTICAL COMPOSITION comprising at least one of the 1,2,3-triazole compounds, or one of their salts, represented by the general formula VIII:

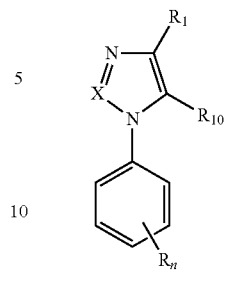

(VIII)

where:
  where X is "N" and the radicals of the triazole ring are represented by:
    $R_1=CF_2R_6$;
    $R_6=R_{10}$=alkyl; and
  where radical $R_n$ can be located in any one or in more than one of the carbon atoms of the aromatic ring and is represented by a halogen, thus "n" can vary from 1 to 5; and
  a pharmaceutically acceptable carrier.

5. THE PHARMACEUTICAL COMPOSITION according to claim 4 wherein the compounds 1,2,3-triazole are selected among:
  1-(3-chlorophenyl)-4-difluoromethyl-1H-1,2,3-triazole; and
  1-(3,5-dichlorophenyl)-4-difluoromethyl-1H-1,2,3-triazole;
  or one of their salts.

6. THE PHARMACEUTICAL COMPOSITION according to claim 4 wherein the compounds 1,2,3-triazole are selected among:
  (AND)-4-chloride-N-((1-(4-chlorophenyl)-1H-1,2,3-triazole-4-il) methylene)benzenamine; and,
  (AND)-4-bromo-N-((1-(4-bromophenyl)-1H-1,2,3-triazole-4-il) methylene)benzenamine, or one of their salts.

7. A PHARMACEUTICAL COMPOSITION according to claim 4 wherein the composition is in the pharmaceutical form of solution, suspension, emulsion, ointment, cream, gel, tablet and/or capsule.

8. THE PHARMACEUTICAL COMPOSITION according to claim 4 wherein the composition is in the pharmaceutical formulation for oral, topical and/or injection form.

9. A PHARMACEUTICAL COMPOSITION, comprising a therapeutically effective amount of the compound of claim 1 and a pharmaceutically acceptable carrier.

* * * * *